(12) United States Patent
la Thangue et al.

(10) Patent No.: US 7,238,493 B2
(45) Date of Patent: Jul. 3, 2007

(54) ACETYLATION OF PRB BY P300 ASSAY METHOD FOR COMPOUNDS WHICH MODULATE THIS PROCESS

(75) Inventors: Nicholas Barrie la Thangue, Abingdon (GB); Ho Man Chan, Boston, MA (US)

(73) Assignee: The University Court of the University of Glasgow, Glasgow, Strathclyde (GB)

( * ) Notice: Subject to any disclaimer, the term of this patent is extended or adjusted under 35 U.S.C. 154(b) by 283 days.

(21) Appl. No.: 10/344,243

(22) PCT Filed: Aug. 9, 2001

(86) PCT No.: PCT/GB01/03597

§ 371 (c)(1),
(2), (4) Date: Aug. 5, 2003

(87) PCT Pub. No.: WO02/14863

PCT Pub. Date: Feb. 21, 2002

(65) Prior Publication Data

US 2004/0048242 A1    Mar. 11, 2004

(30) Foreign Application Priority Data

Aug. 11, 2000  (GB) ................. 0019863.0

(51) Int. Cl.
*C12Q 1/00*      (2006.01)
*C12C 1/02*      (2006.01)
*C12C 1/04*      (2006.01)
*G01N 33/573*    (2006.01)

(52) U.S. Cl. ............ 435/7.3; 435/7.7; 435/7.91; 435/325; 435/7.6; 424/233.1

(58) Field of Classification Search ............ 435/4, 435/7.4, 7.6, 7.7, 7.71, 7.72, 7.9, 7.91, 3; 424/233.1
See application file for complete search history.

(56) References Cited

FOREIGN PATENT DOCUMENTS

| EP | 1 050 581 A1 | 8/2000 |
| JP | WO 99/36532  | 7/1999 |

OTHER PUBLICATIONS

Morris et al. Nature cell Biology 2000, vol. 2, pp. 232-239.*
Heidi et al. J. Virol. 1995, vol. 69, No. 12, pp. 7917-7924.*
Chan et al. Nature cell Biology Jul. 2001, vol. 3, pp. 667-674.*
Goodman et al., *CBP/p300 in cell growth, transformation, and development*; Genes & Development 14:pp. 1553-1577; XP-002219086.
Chan et al., *Acetylation control of the retinoblastoma tumour-suppression protein*; Abstract; Nature Cell Biology, Jul. 2001, 1 page, abstract only.

* cited by examiner

*Primary Examiner*—Bruce Campell
*Assistant Examiner*—Bao Qun Li
(74) *Attorney, Agent, or Firm*—Harness, Dickey & Pierce, P.L.C.

(57) ABSTRACT

The present invention is based upon the finding that the protein p300 has acetylation activity which is directed to the retinoblastoma tumour suppressor protein pRb by the presence in the cell of the adenovirus E1A protein. This represents a target for modulators of the cell cycle, to which end the invention provides an assay for a modulator of acetylation of pRb by p300, which comprises: a) bringing into contact a p300 protein a pRb protein and a putative modulator compound under conditions where the p300 protein, in the absence of said modulator is capable of acetylating the pRb protein; b) providing conditions for acetylation of said pRb protein; and c) measuring the degree of inhibition of acetylation caused by said modulator compound.

7 Claims, 14 Drawing Sheets ii) Acetylation i) Protein

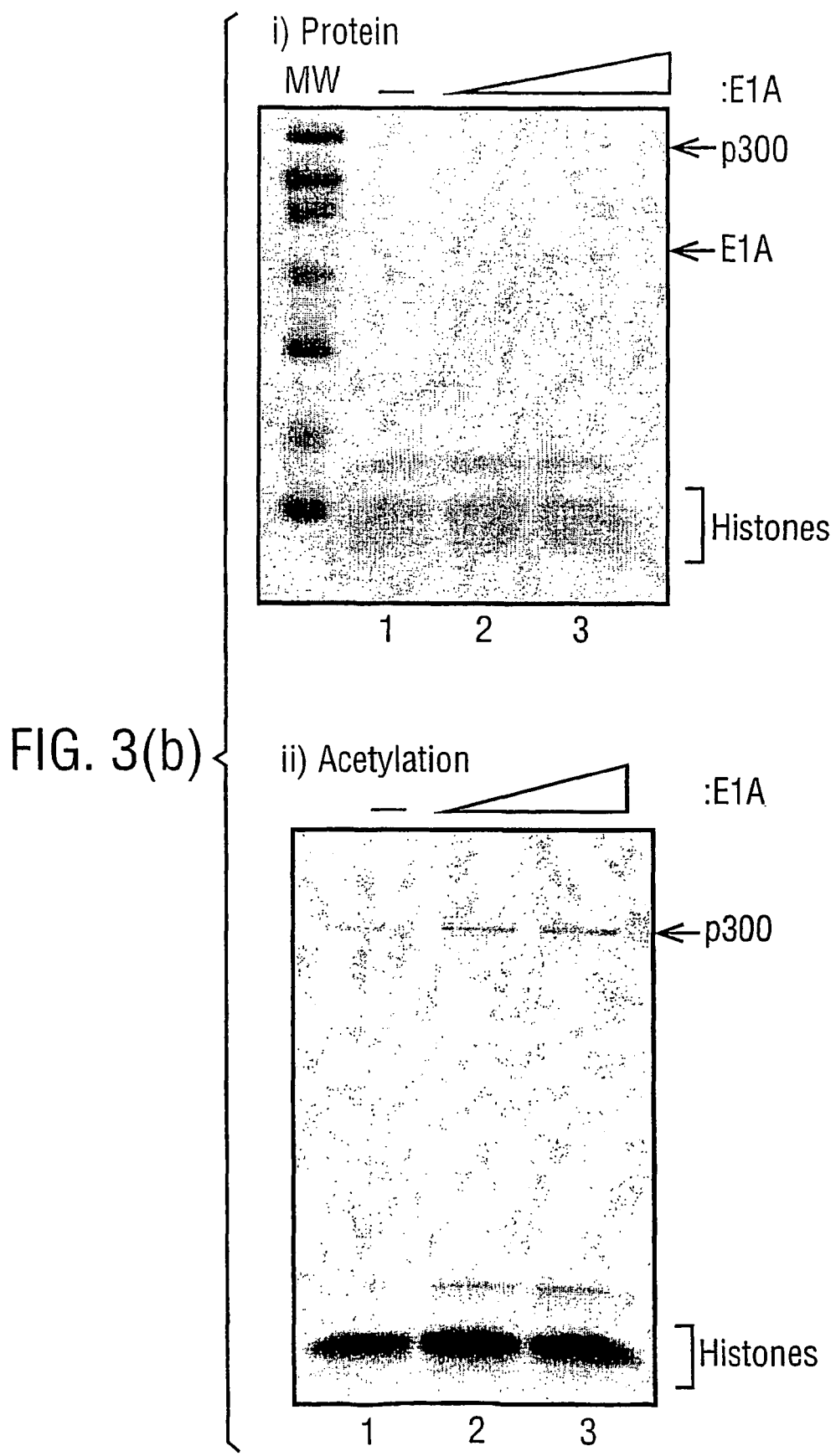

FIG. 5(b)

ACETYLATION OF PRB BY P300 ASSAY METHOD FOR COMPOUNDS WHICH MODULATE THIS PROCESS

CROSS-REFERENCE TO RELATED APPLICATIONS

This application is a U.S. national stage filing under 35 U.S.C. § 371 of international application PCT/GB01/03597, filed Aug. 9, 2001, which claims priority of Great Britain application 0019863.0 filed Aug. 11, 2000.

The present invention relates to the finding of a novel interaction between the proteins p300 and pRb, assays based upon this interaction and novel compounds obtainable by such assay methods.

BACKGROUND TO THE INVENTION.

The product of the retinoblastoma tumour suppressor gene, pRb, mediates control of the G1 to S phase transition by interacting with growth-regulating transcription factors, such as the E2F family [1, 2]. The Rb gene is frequently mutated in tumour cells, and can be inactivated through the physical association with viral oncoproteins such as adenovirus E1A [3]. Post-translational phosphorylation control of pRb by G1 cyclin-dependent kinases plays an important role in regulating pRb activity [4]. The p300/CBP transcriptional co-activator proteins are endowed with histone acetyltransferase (HAT), which is involved in regulating chromatin [6].

SUMMARY

We have identified acetylation as a new level of control in the regulation of pRb. Adenovirus E1A, which sequesters p300/CBP proteins through an N-terminal transformation-sensitive domain3, stimulates the acetylation of pRb by the E1A-dependent recruitment of p300 and pRb into a ternary protein complex. Our data indicate that the acetylation of pRb is specific to the p300/CBP histone acetyl transferases and not a feature of other HATs such as pCAF.

We also observed that the MDM2 oncoprotein can overcome the control of E2F by pRb [7, 8], and our results show that MDM2 preferentially binds to the acetylated form of pRb. Furthermore, acetylation and phosphorylation appear to be distinct levels of control that act on pRb activity. The acetylation of pRb by p300, and the influence on the interaction between MDM2 and pRb, defines a new level of cell cycle control. Moreover, these observations establish a novel relationship between p300, pRb and acetylation in which oncoprotein E1A acts to recruit and target a cellular HAT activity to pRb to effect the loss of pRb-dependent growth control.

Thus, the tumour suppressor pRb is acetylated by the p300 protein, and this acetylation has downstream consequences on the activity of pRb, both in its ability to be phosphorylated by protein kinases, and its ability to interact with the protein MDM2. In consequence, the acetylation of pRb appears to be an event which leads to cell cycle progression so that inhibition of this event provides a target for inhibition of cell proliferation.

Thus in a first aspect the present invention provides an assay for a modulator of acetylation of pRb by p300, which comprises:

a) bringing into contact a p300 protein, a pRb protein and a putative modulator compound under conditions where the p300 protein, in the absence of said modulator is capable of acetylating the pRb protein; and b) providing conditions for acetylation of said pRb protein; and c) measuring the degree of inhibition of acetylation caused by said modulator compound.

In a further aspect, the invention provides compounds obtainable by such an assay, for example peptide compounds based on the portions of p300 or pRb which interact with each other in order to provide acetylated pRb.

The assay of the invention may be performed in vitro using isolated, purified or partially purified p300 and pRb proteins, or in cell free or cellular systems.

BRIEF DESCRIPTION OF THE DRAWINGS

FIGS. 3a-c show adenovirus E1A augments the p300-dependent acetylation of the pRb protein.

FIGS. 5a-b shows functional effects of pRb acetylation.

DETAILED DESCRIPTION

Figure 1A:
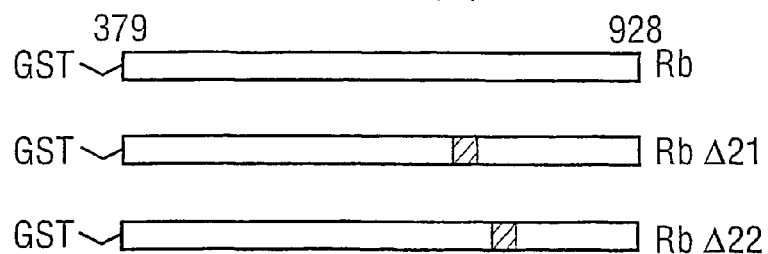
FIGS. 1a-e shows that the retinoblastoma protein is modified by acetylation.
Figure 1B:
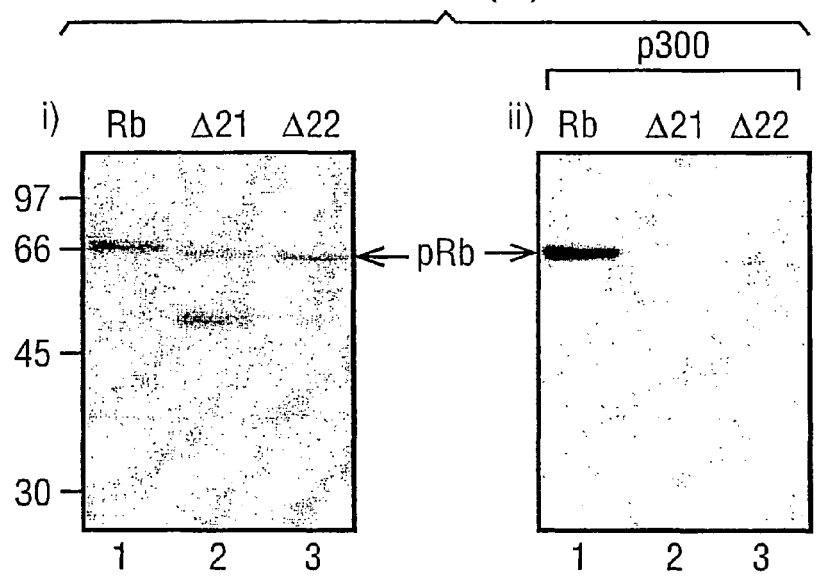

P300.

"p300" is a co-activator protein which has histone acetyltransferase activity, and has been widely studied in the art. p300 is described for example by Eckner et al, 1994 (Genes Dev., 8(8); 869-84). For the purposes of the present invention, reference to p300 refers to human allelic and synthetic variants of p300, and to other mammalian variants and allelic and synthetic variants thereof, as well as fragments of said human and mammalian forms of p300, and its related family member CBP (reviewed in R H. Goodman and S Smolik Genes Dev. (2000) 14: 1553-1577.) Reference herein to p300 is intended to include p300/CBP unless the context is clearly otherwise.

Human p300 has been cloned and sources of the gene can be readily identified by those of skill in the art. Its sequence is available as Genbank accession numbers A54277. Other mammalian p300s are also available, such as murine p300 (accession number AAB31182). P300 gene sequences may also be obtained by routine cloning techniques, for example by using all or part of the human p300 gene sequence as a probe to recover and to determine the sequence of the p300 gene in other species. A wide variety of techniques are available for this, for example PCR amplification and cloning of the gene using a suitable source of mRNA (e.g. from an embryo or a liver cell), obtaining a cDNA library from a mammalian, vertebrate, invertebrate or fungal source, e.g. a cDNA library from one of the above-mentioned sources, probing said library with a polynucleotide of the invention under stringent conditions, and recovering a cDNA encoding all or part of the p300 protein of that mammal.

Suitable stringent conditions include hybridization on a solid support (filter) overnight incubation at 42 C in a solution containing 50% formamide, 5×SSC (750 mM NaCl, 75 mM sodium citrate), 50 mM sodium phosphate (pH 7.6), 5× Denhardt's solution, 10% dextran sulphate and 20 µg/ml salmon sperm DNA, followed by washing in 0.03M sodium chloride and 0.03M sodium citrate (i.e. 0.2×SSC) at from about 50 C to about 60 C). Where a partial cDNA is obtained, the full length coding sequence may be determined by primer extension techniques.

A further approach is to use the above-identified sequences as query sequences to search databases for homologous gene sequences or partial gene sequences (particularly ESTs). Matches identified may be examined and where an actual or putative p300 sequence is found, the gene recovered by physical cloning using, for example PCR and RACE-PCR based on the sequence of the match.

Although wild-type p300 is preferred, and variants of p300 which still retain the ability to acetylate the pRb may also be used. Such variants will generally be based on wild-type mammalian p300s and have a degree of amino acid identity which is desirably at least 70%, preferably at least 80%, 90%, 95% or even 98% identity to a wild type mammalian p300, preferably to human p300.

It is not necessary to use the entire p300 proteins (or variants thereof) for assays of the invention. Fragments of the p300 may be used provided such fragments retain the ability to acetylate the target domain of the pRb. Examples of two such fragments, p3001195-1673 and p3001135-2414 are provided in the accompanying examples. This demonstrates that a fragment of at least about 450 amino acids or more, such as at least about 1000 amino acids can be made with this ability. Those of skill in the art will be able to construct similar fragments using routine skill and knowledge, e.g. by PCR subcloning, in a manner analogous to that illustrated below for the production of pRb fragments.

The ability of suitable variants or fragments to acetylate pRb (or a fragment thereof) may be tested using routine procedures such as those described in the accompanying examples.

Reference herein to a p300 protein includes the above-mentioned variants and fragments which are functionally able to acetylate pRb unless the context is explicitly to the contrary.

pRb Protein.

The pRb protein is a pocket protein involved in the regulation of the cell cycle and has been widely studied in the art. pRb is described for example by Lee et al, 1987, Science, 235(4794); 1394-9. For the purposes of the present invention, reference to pRb refers to human allelic and synthetic variants of pRb, and to other mammalian variants and allelic and synthetic variants thereof, as well as fragments of said human and mammalian forms of pRb.

Human pRb has been cloned and sources of the gene can be readily identified by those of skill in the art. Its sequence is available as Genbank accession number P06400. Other pRbs are also available, such as murine pRb (Genbank accession number P13405), rat pRB (Genbank P33568), chicken (CAA51019) and salamander (CAA70428). pRb gene sequences may also be obtained by routine cloning techniques, for example by using all or part of the human pRb gene sequence as a probe to recover and to determine the sequence of the pRb gene in other species. A wide variety of techniques are available for this, for example PCR amplification and cloning of the gene using a suitable source of mRNA (e.g. from an embryo or a liver cell), obtaining a cDNA library from a mammalian, vertebrate, invertebrate or fungal source, e.g a cDNA library from one of the above-mentioned sources, probing said library with a polynucleotide of the invention under stringent conditions, and recovering a cDNA encoding all or part of the pRb protein of that mammal.

Suitable stringent conditions include those described above in relation to p300. Where a partial cDNA is obtained, the full length coding sequence may be determined by primer extension techniques.

A further approach is to use the above-identified sequences as query sequences to search databases for homologous gene sequences or partial gene sequences (particularly ESTs), as described above in relation to p300.

Although wild-type pRb is preferred, and variants of pRb which still retain the ability to be acetylated by p300 may also be used. Such variants will generally be based on wild-type mammalian pRbs and have a degree of amino acid identity which is desirably at least 70%, preferably at least 80%, 90%, 95% or even 98% identity to a wild type mammalian pRb, preferably to human pRb.

It is not necessary to use the entire pRb proteins (or variants thereof) for assays of the invention. Fragments of the pRb may be used provided such fragments retain the ability to be acetylated by p300. Our data indicate that the C-terminal region of pRb is the target for acetylation by the p300 protein. Thus as exemplified in the accompanying examples, fragments which contain this region may be used in assays of the invention. Examples of such fragments include those in the accompanying examples spanning the residues lysine 873 and 874 of the human pRb sequence. This demonstrates that fragments comprising these two residues which are as little as about 40 amino acids or more, such as 50, 60 or 80 amino acids or more can be made and used in an assay of the invention. There is also evidence that similar sized fragments comprising the region 794-829 may be acetylated. In any event, such fragments will comprise at least one target lysine residue for acetylation.

Those of skill in the art will be able to construct similar fragments using routine skill and knowledge, e.g. by PCR subcloning, in a manner analogous to that illustrated below for the production of pRb fragments. The ability of suitable variants or fragments to be acetylated by p300 (or a fragment thereof) may be tested using routine procedures such as those described in the accompanying examples. Reference herein to a pRb protein includes the above-mentioned variants and fragments which are functionally able to be acetylated by pRb unless the context is explicitly to the contrary.

The assays of the invention preferably use the same mammalian source pRb as the p300.

p53 p53 refers to the tumour suppressor gene or its encoded amino acid sequence of as reported, for example, by Matlashewski et al (EMBO J. 13; 3257-62, 1984) or Lamb and Crawford (Mol. Cell. Biol. 5; 1379-85, 1986). These sequences are available on Genbank. Wild-type human p53 protein includes a proline/arginine polymorphism at amino acid 72, reflecting a corresponding polymorphism in the gene. Reference to p53 further includes mutated forms of p53 as found in many tumour cells. Such mutations include point mutations, for example from 1 to 10, e.g from 1 to 5 point mutations (which point mutations result in a change to the amino acid sequence) to the wild-type sequences. It further includes fragments of wild-type and mutated p53 which retain the ability to be a substrate for acetylation by p300. Such fragments are preferably at least 20, more preferably at least 30 and most preferably at least 50 amino acids in size.

MDM2

The sequence of the human MDM2 oncoprotein may be found by reference to Genbank accession number Q00987. Other mammalian MDM2 proteins are known, for example mouse (Genbank P23804), horse (P56273), dog (P56950) and hamster (Q60624), as well as non-mammalian homologues such as chicken (AAF04192), *xenopus* (P56273) and zebrafish (O42354). Where assays of the invention involve the use of an MDM2 oncoprotein, this may be a wild-type MDM2 or a variant which is capable of binding to acetylated pRB. Such variants will generally be based on wild-type mammalian MDM2s and have a degree of amino acid identity which is desirably at least 70%, preferably at least 80%, 90%, 95% or even 98% identity to a wild type mammalian MDM2, preferably to human MDM2. These include variants obtainable from other species, in a manner analogous to that described above for p300 and pRb.

Amino Acid Identity.

The percentage homology (also referred to as identity) of DNA and amino acid sequences can be calculated using commercially available algorithms. The following programs (provided by the National Center for Biotechnology Information) may be used to determine homologies: BLAST, gapped BLAST and PSI-BLAST, which may be used with default parameters. The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

Where default parameters or other features of these programs are subject to revision, it is to be understood that reference to the programs and their parameters are as of the priority date of the instant application.

Assay formats.

Assays according to the present invention may be provided in any suitable format. Desirably, the assays will be adapted to provide for a high throughput format, such that a large number of putative modulator compounds may be screened simultaneously and/or sequentially, using automated robotic technology which is available in the art for methodology of this nature. Assays of the invention may be used to screen for inhibitors of acetylation, in which case the measured degree of acetylation will be reduced by the presence of the modulator when compared to a control in which the modulator is absent.

In one format, labelled acetyl CoA is provided together with p300 and pRb proteins in appropriate concentrations in a buffer which provides for acetylation in the absence of an inhibitory modulator. The proteins are incubated in the presence of a putative modulator and the amount of acetylation is determined, e.g. by recovering the pRb protein and observing or measuring the amount of labelled acetate incorporated into the pRb.

Alternatively, the acetylation of pRb may be determined using antibodies which bind to acetylated lysine residues on the pRb. Such antibodies are commercially available, including those used in the accompanying examples.

The amount of acetylation in the presence of a modulator may be compared to the amount obtained in the absence of a modulator. Such a control may be performed in parallel with the assay, or be a standardised control value to which the amount is compared. In a high throughput format, the skilled person may opt to dispense with a negative (i.e. no modulator present) control and instead select a pre-determined percentage of the compounds screened, wherein these compounds are at the top end of the distribution of activity of all the compounds in a set of compounds being screened.

The assay of the invention may also be conducted in cells in culture or in cell lysates. In such circumstances, the cells may express p300 or pRb naturally, or contain a recombinant DNA construct from which the p300 or pRb is expressed.

Desirably, at least the pRb protein is in the form of a fusion protein comprising the pRb and a detectable tag, such as GST or a his tag (many others are known as such in the art), so that the pRb may be isolated via the tag—e.g. by immuno-precipitation or using glutathione-Sepharose (TM) beads, thus allowing accurate quantitation of pRb acetylation.

There are a number of additional components which may be used in the assays of the invention. For example, we have found that the adenovirus protein E1A, which binds both p300 and pRb, provides for enhanced acetylation of pRb by p300, at least up to a concentration of E1A which favours the formation of a ternary E1A-p300-pRb complex over binary E1A-p300 and E1A-pRb complexes. Thus E1A may be provided to assays of the invention in order to enhance the acetylation of pRb. The E7 protein of HPV is also known to bind to both p300 and pRb, and may also be used to provide a similar effect. The HPV E7 protein may be from any HPV species, particularly those associated with cervical cancer, such as HPV 16. Similarly, other viral oncoproteins which bind at least one of p300 or pRb, preferably both, may also be used.

Moreover, the up-regulation in acetylation of pRb by the formation of a ternary complex may be a normal cellular process. Accordingly, a cellular protein may be used in place of these viral oncoproteins to achieve the same effect. For example, we have found that the cellular protein "JMY" described in SEQ ID NO:2 of WO99/20752, the disclosure of which is incorporated herein by reference, binds p300 in a region which is also responsible for E1A binding. JMY may be used in place of E1A to provide a binding complex of p300, pRb and JMY.

We have also found that pRb when acetylated binds to the MDM2 oncoprotein more strongly than when not acetylated. Thus the assay of the invention may incorporate MDM2 and the output of the assay may be measured as the amount of MDM2-pRb binding observed following acetylation of pRb by p300 in the presence or absence of a putative modulator. The MDM2-pRb binding may be determined in any suitable way, for example by immuno-precpitation. precipitation.

The interaction between acetylated pRb and MDM2 gives rise to a further aspect of the invention, since this interaction provides a further target for inhibition of cell cycle progression. Thus there is also provided by the invention an assay for a modulator of cell cycle progression which comprises:

a) bringing into contact an acetylated pRb protein and an MDM2 protein under conditions where, in the absence of modulator, the two proteins bind to each other;

b) providing a putative modulator; and c) determining the degree of modulation of binding of the two proteins caused by said modulator.

By "acetylated pRb" it is meant a pRb protein as defined herein wherein at least one lysine residue is acetylated.

We have also found that acetylation of pRb influences the ability of the cyclin dependent kinase cyclin E/cdk2 to phosphorylate pRb. Thus the amount of acetylation of pRb may be determined indirectly by a subsequent phosphorylation assay, for example by bringing the pRb into contact with cyclin E/cdk2 in the presence of gamma 32P labelled ATP, followed by separation of the pRb and the determination of the amount of labelled phosphate incorporated therein.

In another aspect, we have found that a consequence of E1A binding p300 is that the ability of p300 to acetylate p53 and E2F-1 is compromised. Since p53 is activated by acetylation, the binding of p300 to E1A and the consequent redirection of p300 HAT activity to pRb which results points to a mechanism by which oncoproteins can antagonise the function of p53.

This finding may be used to provide an assay in which p53 acetylation is measured as an end point in an assay for modulators of the interaction between p300 and onconproteins which bind p300, particularly E1A.

Modulator compounds.

The amount of putative modulator compound which may be added to an assay of the invention will normally be determined by trial and error depending upon the type of compound used. Typically, from about 0.01 to 100 nM concentrations of putative modulator compound may be used, for example from 0.1 to 10 nM. Modulator compounds may be those which either agonise or antagonise the interaction. Antagonists (inhibitors) of the interaction are particularly desirable.

Modulator compounds which may be used may be natural or synthetic chemical compounds used in drug screening programmes. Extracts of plants which contain several characterised or uncharacterised components may also be used. Many libraries of natural and synthetic compounds are commercially available for drug screening programs, and these may be bought and used in the assays of the invention.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction between p300 and the pRb.

Other candidate inhibitor compounds may be based on modelling the 3-dimensional structure of p300 and pRb and using rational drug design to provide potential inhibitor compounds with particular molecular shape, size and charge characteristics. Assays of the invention and modulator compounds of the invention have a variety of uses. For example, the task of dissecting the complex pathways of cellular proliferation will be facilitated by the provision of means to promote or inhibit a specific interaction, allowing the effects of other proteins in the pathway to be studied in better detail.

Candidate modulator compounds obtained according to the method of the invention may be prepared as a pharmaceutical preparation. Such preparations will comprise the compound together with suitable carriers, diluents and excipients. Such formulations form a further aspect of the present invention.

Formulations may be prepared suitable for any desired route of administration, including oral, buccal, topical, intramuscular, intravenous, subcutaneous and the like.

Formulations for topical administration to the skin may include ingredients which enhance the permeability of the skin to the peptides. Such formulations may be in the form of ointments, creams, transdermal patches and the like.

Formulations for administration by injection (i.m., i.v., subcutaneous and the like) will include sterile carriers such as physiological saline, optionally together with agents which preserve or stabilise the peptide. Albumin may be a suitable agent.

Formulations of inhibitor compounds in particular may be used in methods of treatment, such as controlling cell proliferation in disease states such as cancer, pre-cancerous cell growth, psoriasis, etc. Compounds obtainable by such an assay form a further aspect of the invention.

All publications, patent applications and sequence accession disclosures cited in this specification are herein incorporated by reference as if each individual publication, patent application or sequence were specifically and individually indicated to be incorporated by reference.

The following examples illustrate the invention.

A. Acetylation of pRb In Vitro.

Some co-activators, such as p300/CBP, are endowed with HAT activity5, 6. To evaluate whether pRb could be acetylated by the p300 HAT, we assessed if a GST-pRb fusion protein was acetylated in vitro. We found that GST-pRb could be acetylated by p300 in a fashion that is influenced by the integrity of the pocket domain, as the acetylation of two pocket mutants (pRbΔ21 and Δ22) isolated from human tumour cells 9 was very much reduced (FIGS. 1a and b). A similar analysis using enzymatically active P/CAF10 failed to provide evidence for pRb acetylation mediated by the P/CAF HAT activity, suggesting that acetylation of pRb was HAT-specific.

B. Acetylation of pRb in SAOS2 cells.

Figure 1D:
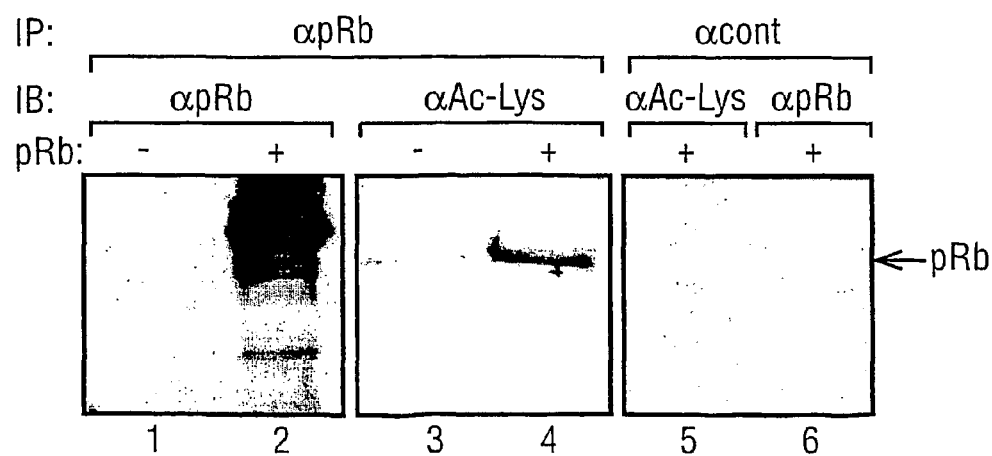
Figure 1C:
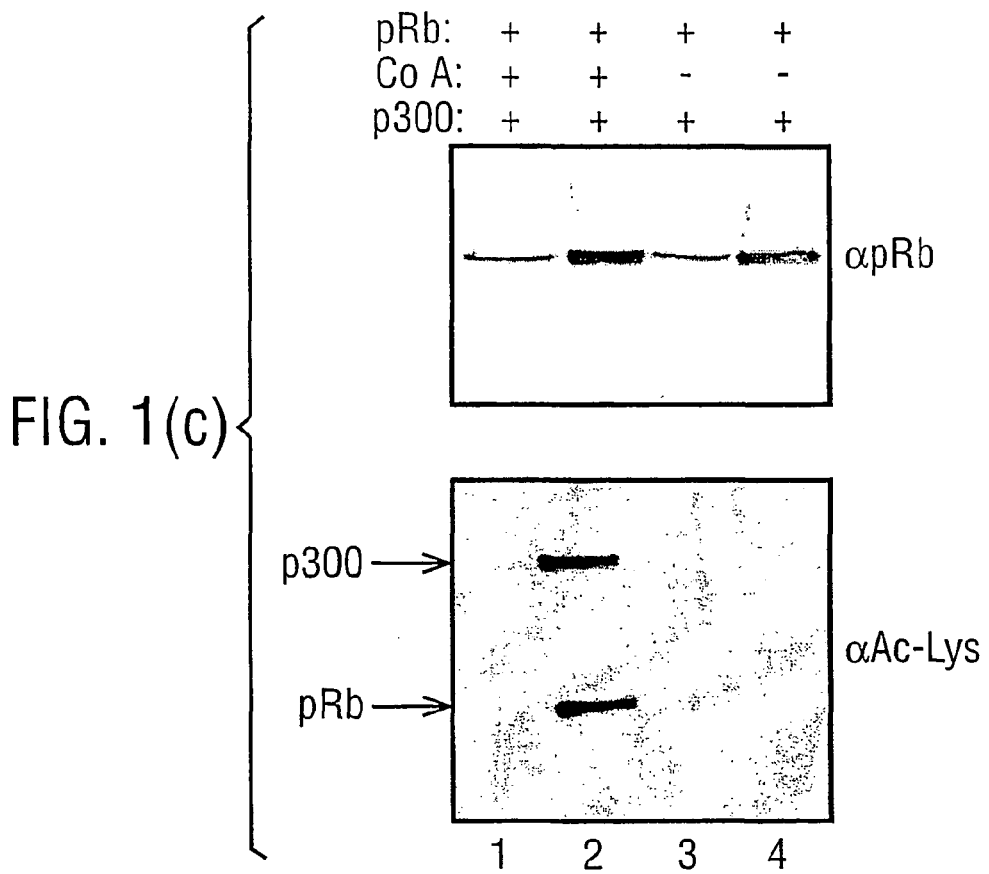

Whilst the above results indicate that pRb can be acetylated, the analysis was based on the effects of the HAT activity observed in vitro and, therefore, it was important to establish that pRb could be acetylated in vivo under physiological conditions. In order to assess pRb acetylation, we used an antibody directed against acetylated lysines which specifically recognised pRb that had been acetylated by the p300 HAT, but failed to bind to unacetylated pRb (FIG. 1c).

Figure 1E:
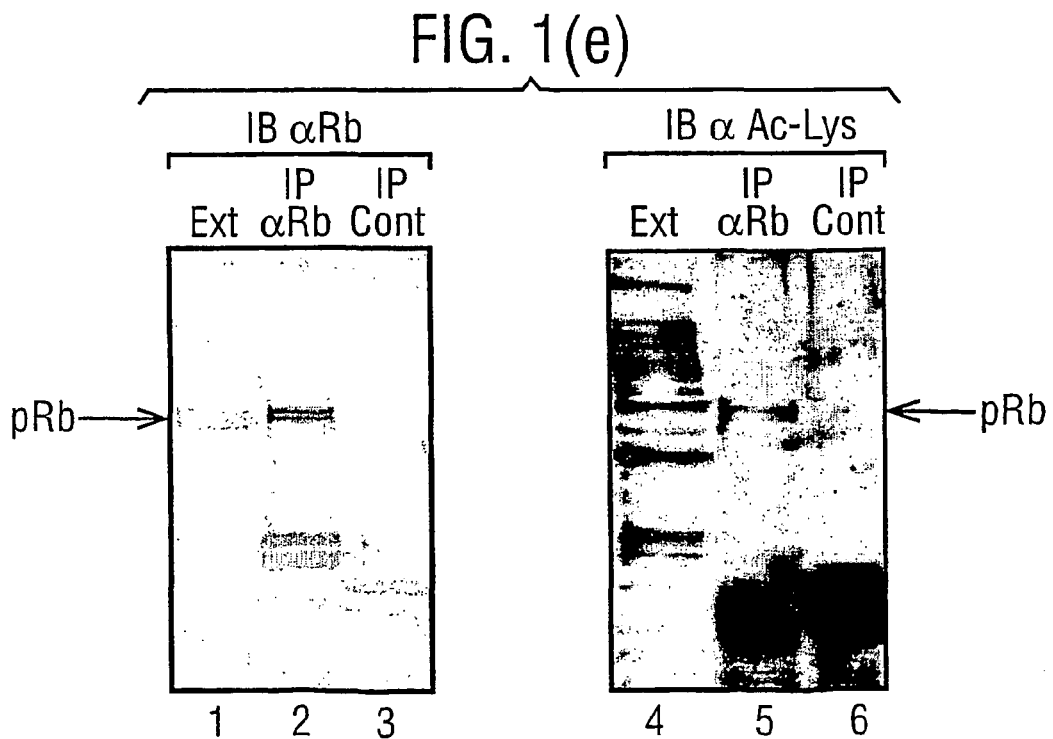

We used this antibody to assess pRb acetylation in cells. To this end, pRb was immunoprecipitated from SAOS2 (Rb−/−) cells transfected with a pRb expression vector, and the immunoprecipitate immunoblotted with the anti-acetylated lysine antiserum, upon which acetylated pRb was apparent (FIG. 1d). Taking a similar approach, this conclusion was substantiated in non-transfected 293 cells where endogenous acetylated pRb was clearly detected (FIGS. 1e and 4d). Overall, these results establish that pRb is physiologically acetylated.

C. Acetylation of pRb is in the C-Terminal Region.

Figure 2A:
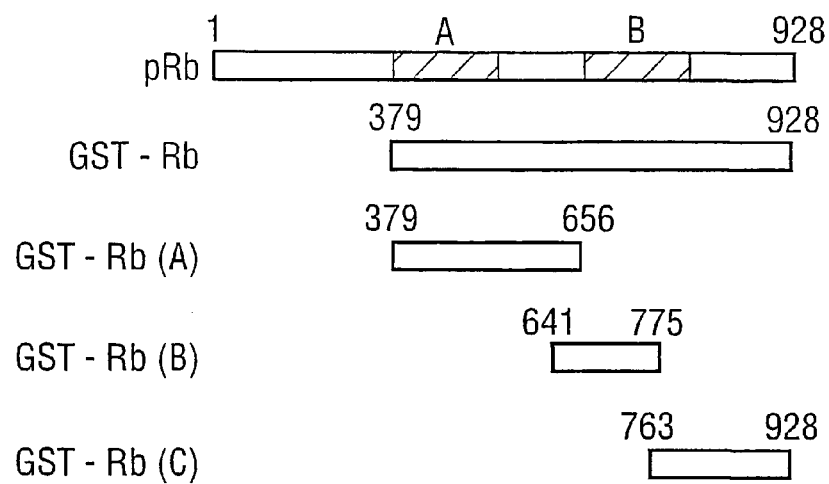
FIGS. 2a-f shows that the C-terminal region of pRb is a major site of acetylation.
Figure 2B:
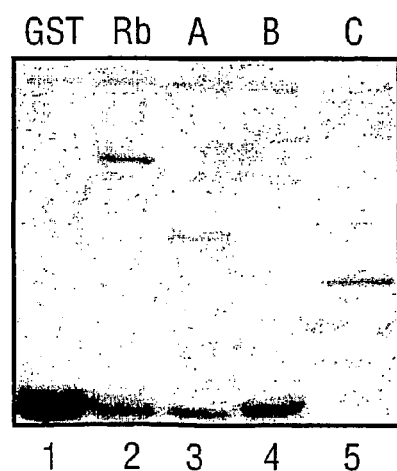
Figure 2B:
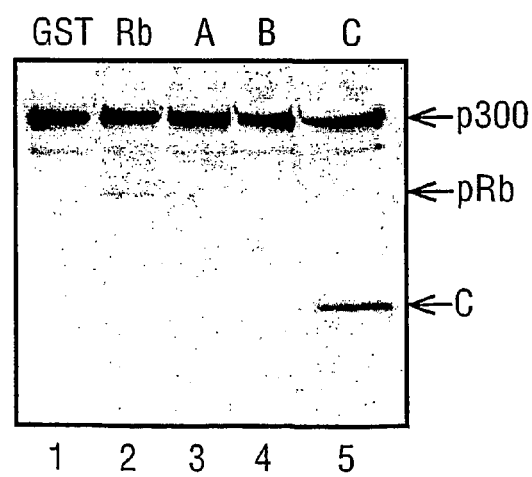
Figure 2C:
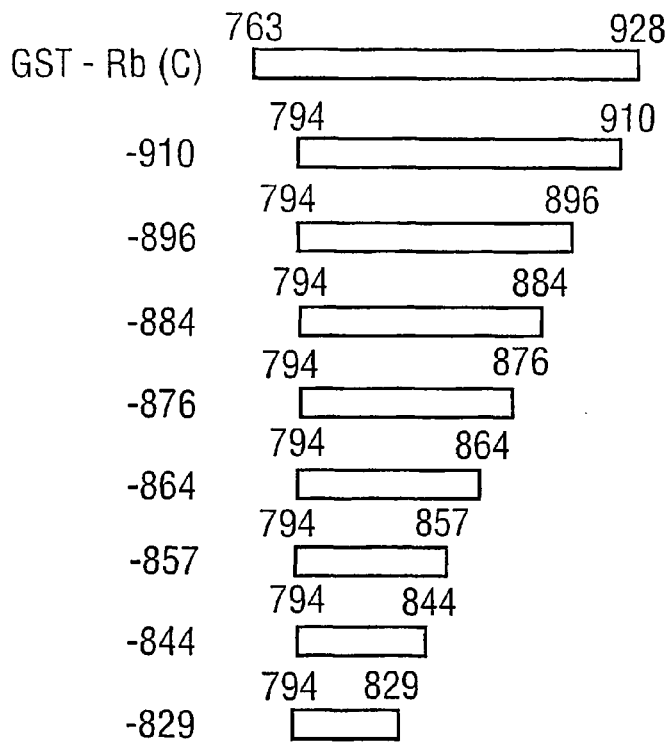
Figure 2F:
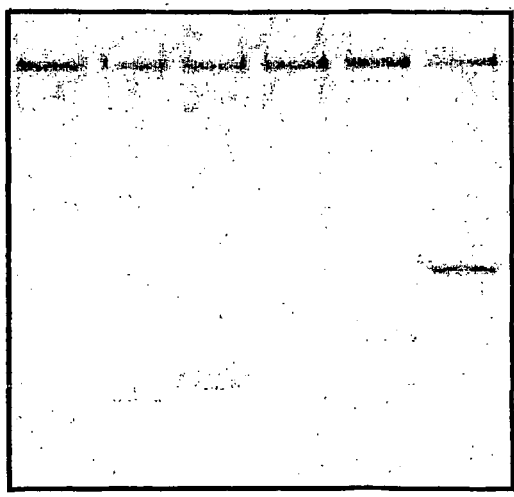
Figure 2E:
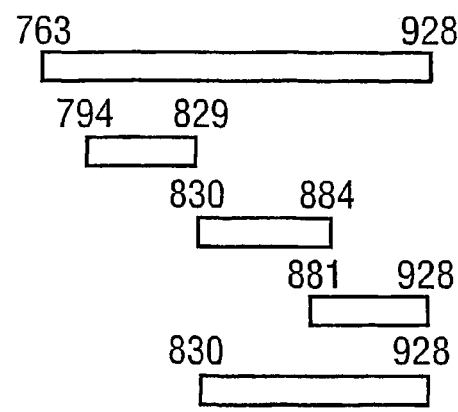
Figure 2D:
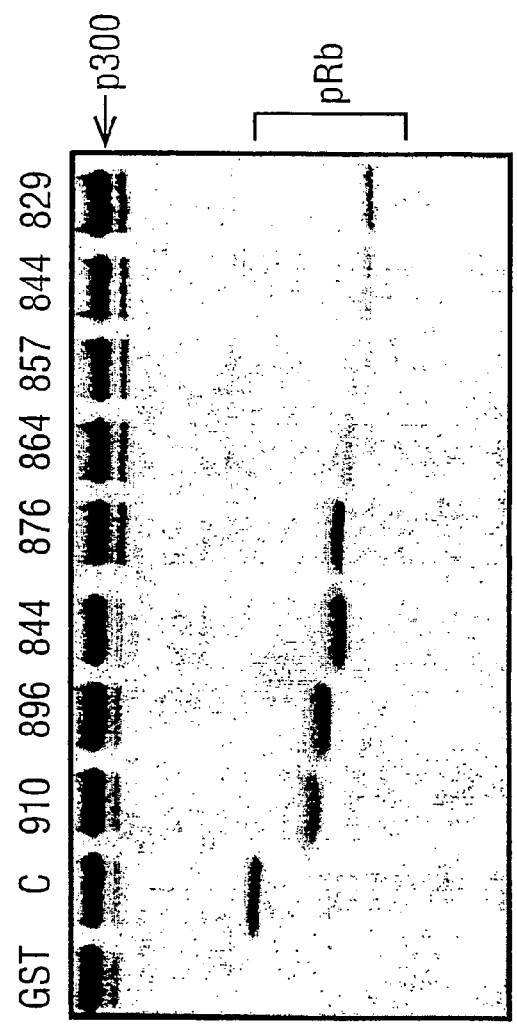
Figure 2D:
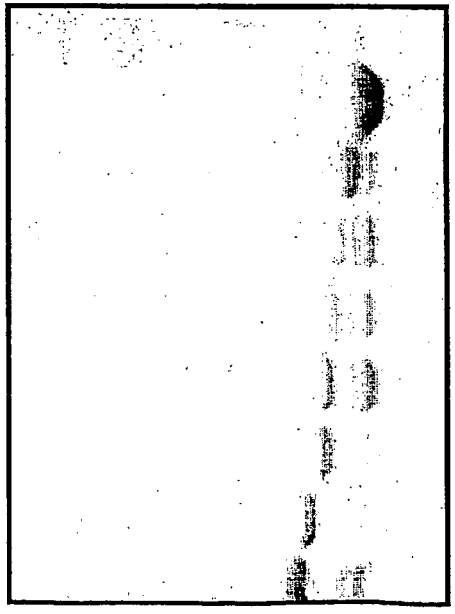

Whilst the acetylation of pRb required the integrity of the pocket region (FIG. 1a), it was nevertheless possible that acetylation in the wild-type protein occurred outside the pocket region, and thus we determined more precisely the region in pRb that could be directly targeted by acetylation. To assess the general region in pRb that is acetylated by p300, we examined the in vitro acetylation status of the two halves of the pocket, together with the C-terminal domain (FIG. 2a). Whilst the A and B pocket domains were poorly acetylated, the C-terminal domain exhibited much stronger acetylation (FIG. 2b), suggesting that this region contains the major sites for acetylation. By studying the acetylation of an extensive panel of mutant derivatives, the major regions of acetylation were mapped to between residue 794 to 829, and 830 to 884 (FIG. 2c). A C-terminal derivative from residue 881 and 928, which contains seven lysine residues, failed to be acetylated (FIGS. 2e and f). Thus, the sites of acetylation occur on lysine residues within the 87 residue region flanked by residue 794 to 880. Altogether, eight lysines occur within this region, and later in this report we identify two lysine residues from this region that are acetylated.

D. The E1A Oncoprotein Enhances Acetylation.

Figure 3A:
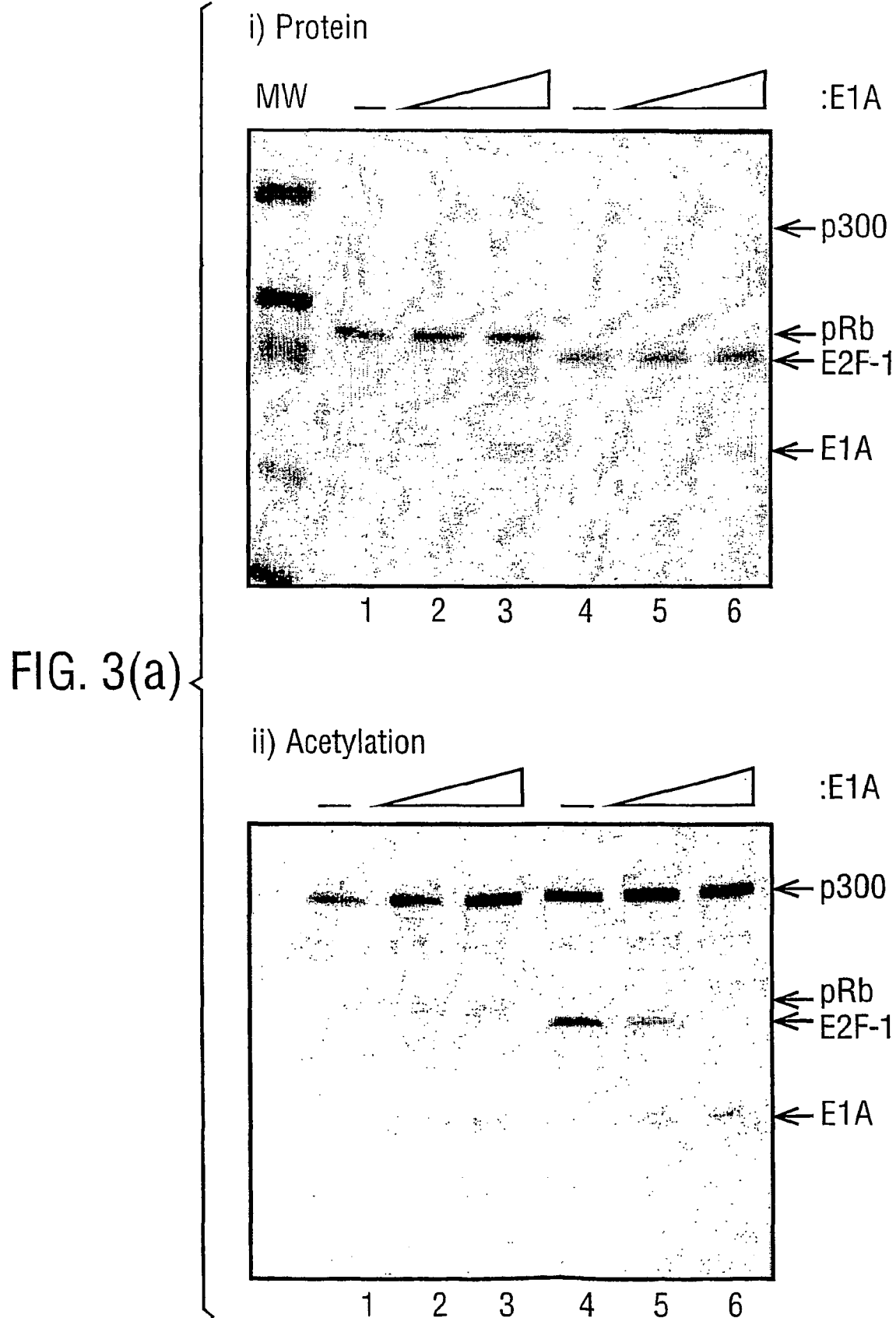
Figure 3C:
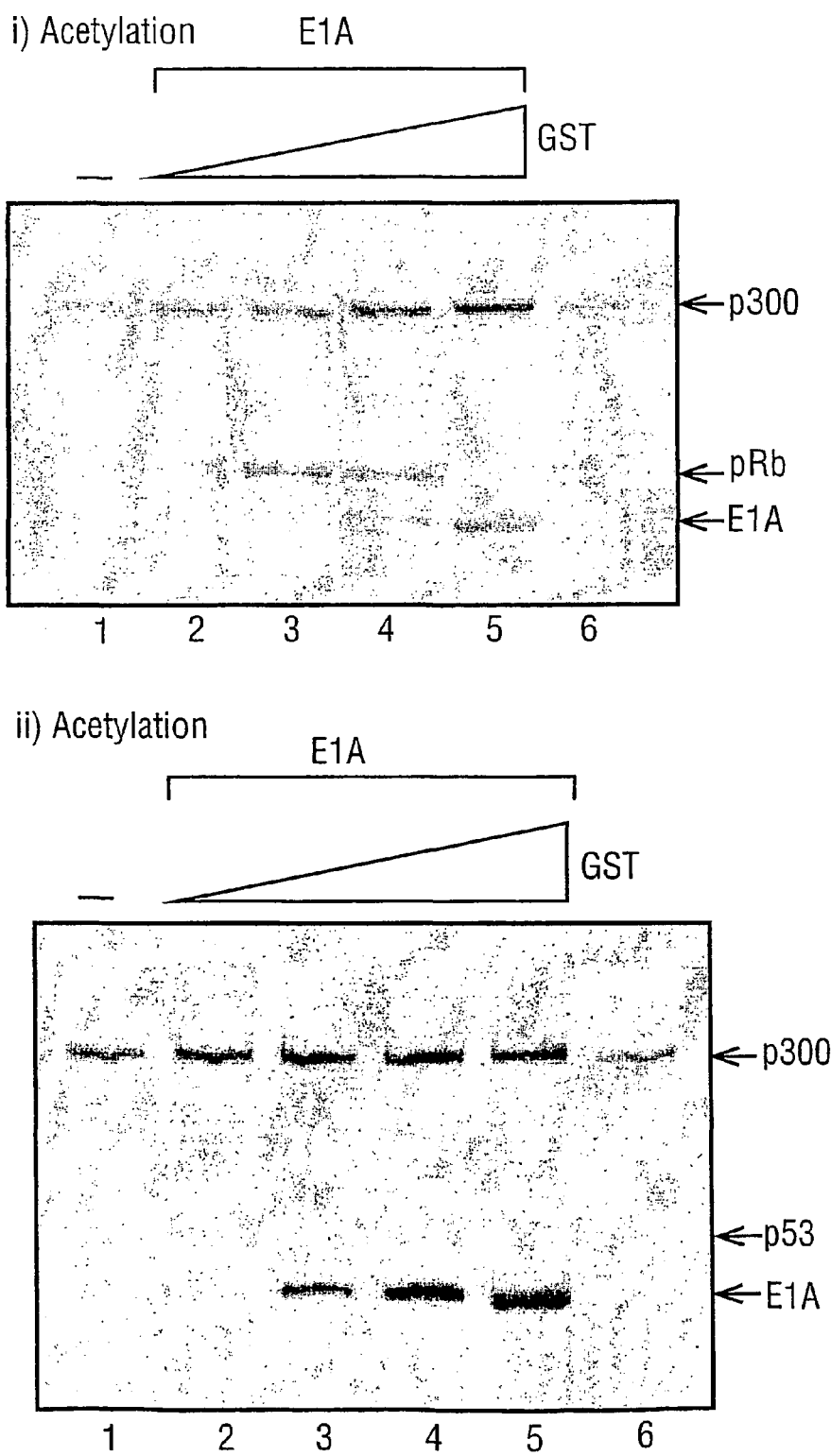

The adenovirus E1A oncoprotein binds to and sequesters a variety of cellular proteins, including pRb and p300 family members, through domains that are necessary for E1A to exert its effects on cellular growth and differentiation 3. The binding of p300/CBP proteins requires an N-terminal domain in E1A, and two domains, referred to as conserved regions (CR) 1 and 2, for binding to pRb3. Given the well-documented interaction of p300 and pRb with E1A, together with the p300-dependent acetylation of pRb described here (FIG. 1), it was of interest to investigate the influence of E1A on the acetylation level of pRb. In order to assess the effect of E1A, recombinant wild-type E1A was titrated into the pRb acetylation reaction, together with p3001135-2414 as the source of HAT, which also harbours the E1A-binding domain for p30011. Upon the addition of E1A protein there was a significant and specific stimulation in pRb acetylation mediated by the p300 HAT (FIG. 3a). This effect was concentration-dependent since at high molar ratios of E1A to p300 and pRb, further increases in E1A levels caused the loss of enhancement of pRb acetylation (FIG. 3ci). Since E1A can bind to both pRb and p300 proteins3, these results are consistent with the idea that E1A stimulates the acetylation of pRb by recruiting pRb and p300 into a ternary complex containing E1A, pRb and p300, thus directing the p300 HAT activity to pRb. The loss of enhancement of pRb acetylation at high levels of E1A may therefore result from E1A forming complexes independently with pRb or p300.

In contrast to its effect upon pRb, the presence of E1A failed to significantly affect p300-autoacetylation, and the p300-dependent acetylation of core histones was marginally affected by E1A (two-fold at most; FIG. 3b). However, the acetylation of the p53 tumour suppressor protein and E2F-1, the activities of which are known to be influenced by acetylation12, 13, 14, 15, was compromised in the presence of E1A (FIGS. 3aii and cii). Overall, these results establish that E1A can alter the p300-dependent acetylation of target protein substrates and, most importantly, augment the level of pRb acetylation.

E. Physical Interaction of E1A with pRb is Required.

Figure 4A:
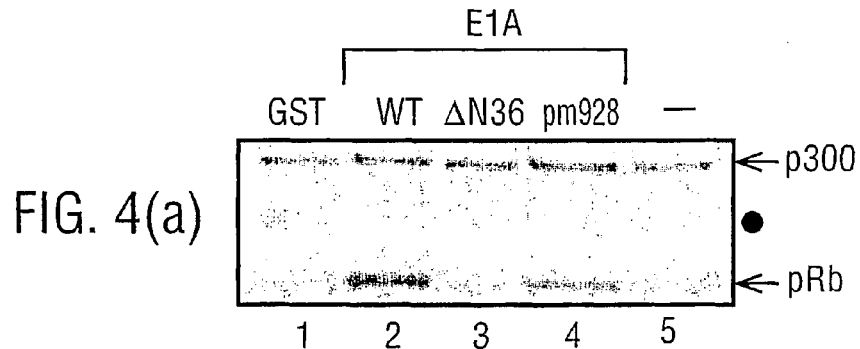
FIGS. 4a-g shows that domains in E1A for p300-dependent acetylation of pRb and acetylated pRb binds to MDM2.
Figure 4B:
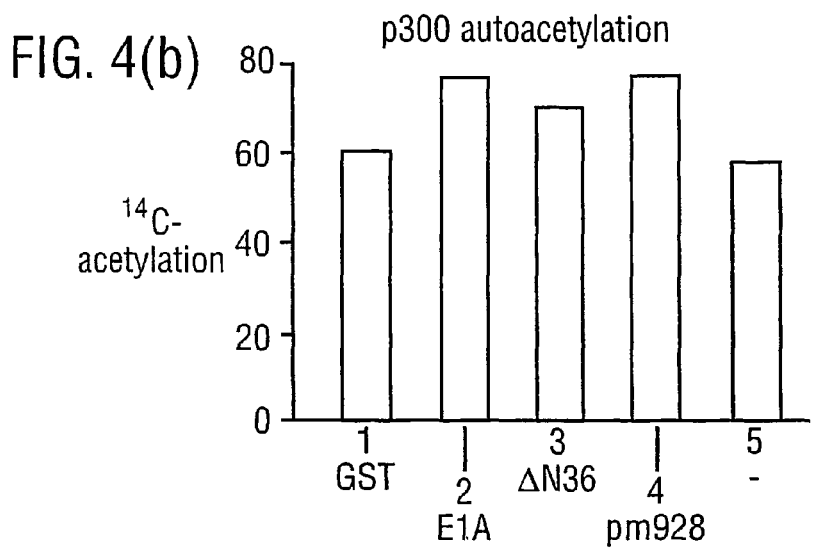
Figure 4C:
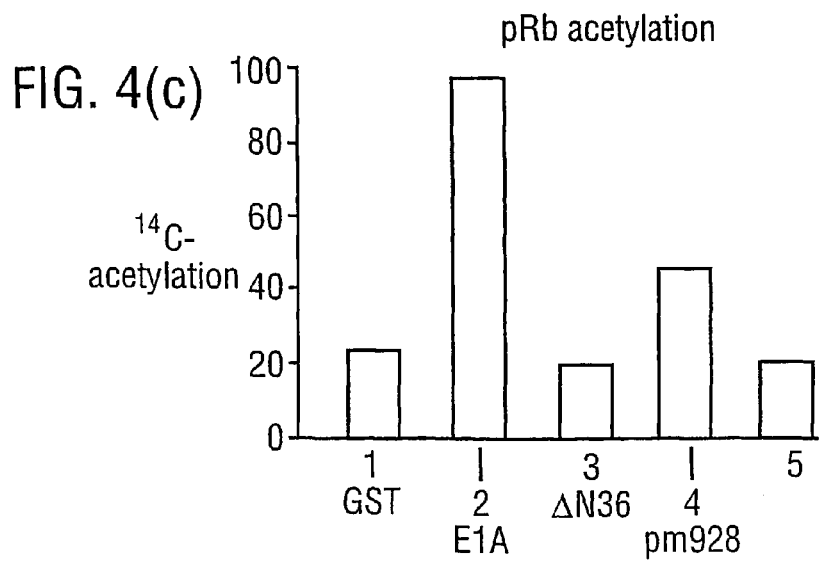
Figure 4D:
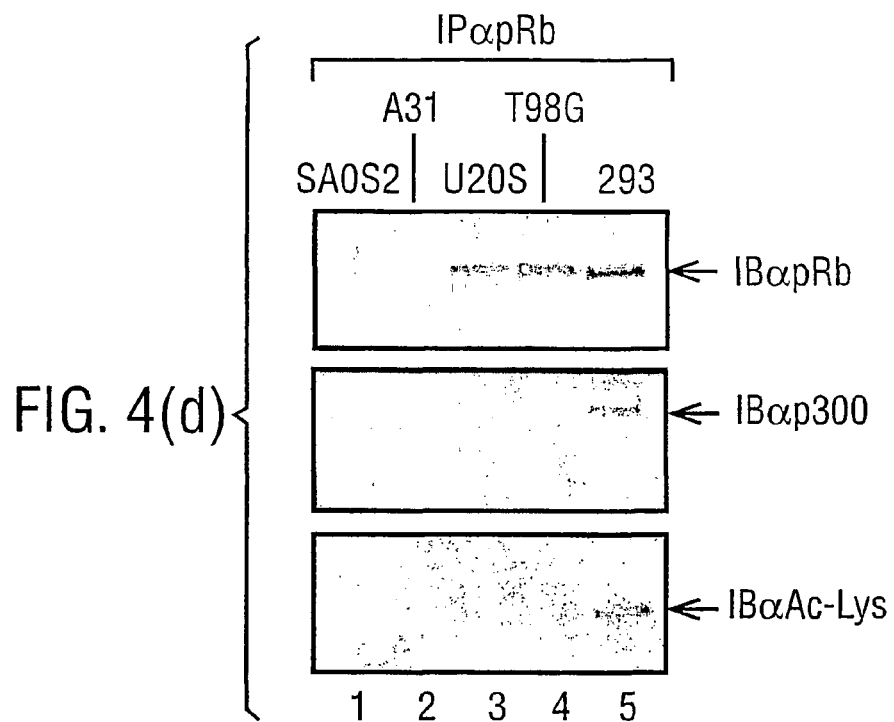

To determine the specificity of the effects on pRb, we assessed the properties of a variety of mutant derivatives in E1A that are compromised in ability to bind either pRb or p300 (FIG. 4a). Mutant E1A proteins that failed to bind pRb, namely ΔCR1, ΔCR2 and pm928, or p300, such as ΔN3616, could not effectively stimulate the p300-dependent acetylation of pRb, whilst there was little effect on the autoacetylation of p300 (FIGS. 4a, b, and c; and data not shown), arguing that a physical interaction between all three proteins is necessary for E1A to stimulate pRb acetylation by the p300 HAT activity.

Moreover, since pRb is acetylated in 293 cells (FIG. 1e), which express E1A17, it was of interest to compare the level of pRb acetylation in 293 cells with other cell-types that do not express E1A. By immunoprecipitation, we found that pRb in 293 cells showed a much higher level of acetylation compared to other cell-types, including U2OS, T98G and C33A (FIG. 4d; and data not shown). Since 293 cells express the E1A protein, the results support the idea that E1A stimulates the acetylation of pRb by p300. A further consistency with this idea was the presence of p300 in the pRb immunoprecipitate, which was also seen in the 293 cell immunocomplex (FIG. 4d).

F. pRb Acetylation Enhances Interaction with MDM2.

Figure 4E:
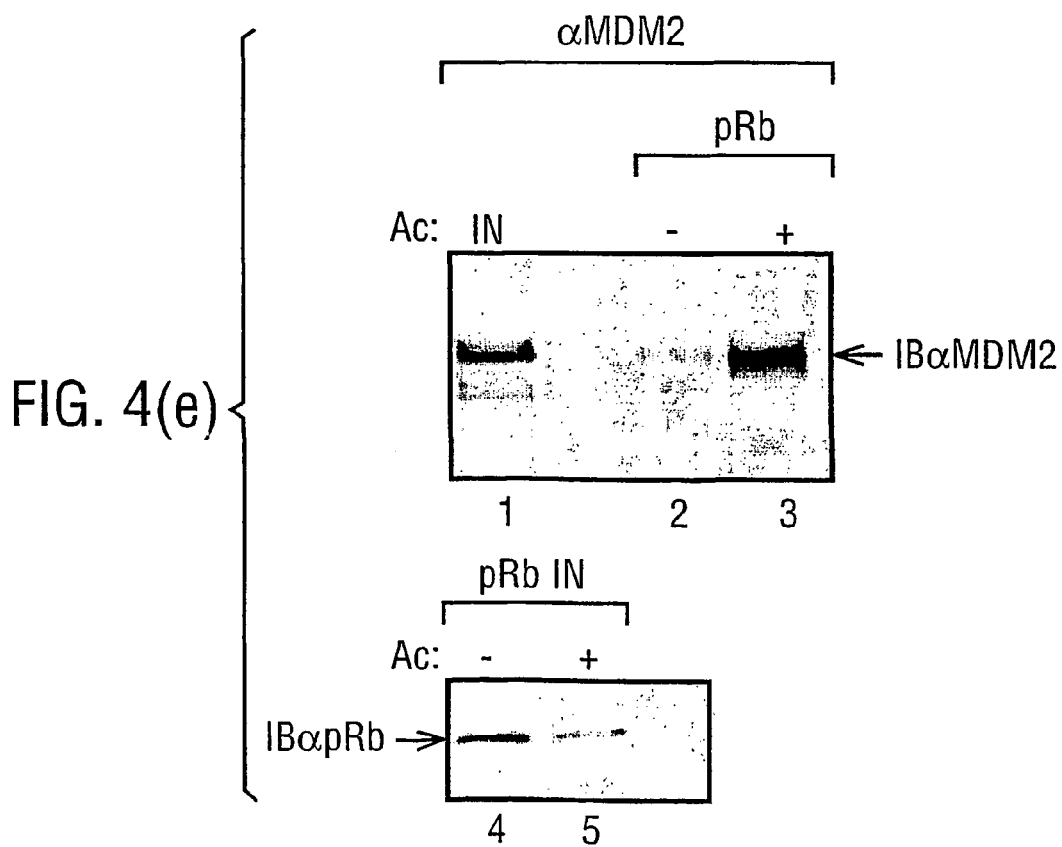

To elucidate the functional importance of pRb acetylation, we were prompted to assess its impact on the MDM2 oncoprotein, which binds to the C-terminal region of pRb and as a result antagonises the pRb-dependent down-regulation of E2F activity7. As expected from previous studies7, in a biochemical assay pRb bound to MDM2 and the minimal region in pRb responsible for the interaction was mapped to within residue 792 to 928 (data not shown). To determine the importance of pRb acetylation in the regulation of MDM2 binding, pRb was acetylated by the p300 HAT and thereafter acetylated pRb purified as described. Then, the binding efficiency of in vitro translated MDM2 was assessed. At equivalent levels of input pRb, we found that the efficiency of binding between MDM2 and acetylated pRb was much greater than to the non-acetylated pRb (FIG. 4e), suggesting that MDM2 preferentially binds to the acetylated form of pRb. Similar experiments performed to evaluate the influence of acetylation on the interaction of pRb with E2F failed to detect any differences.

Figure 4F:
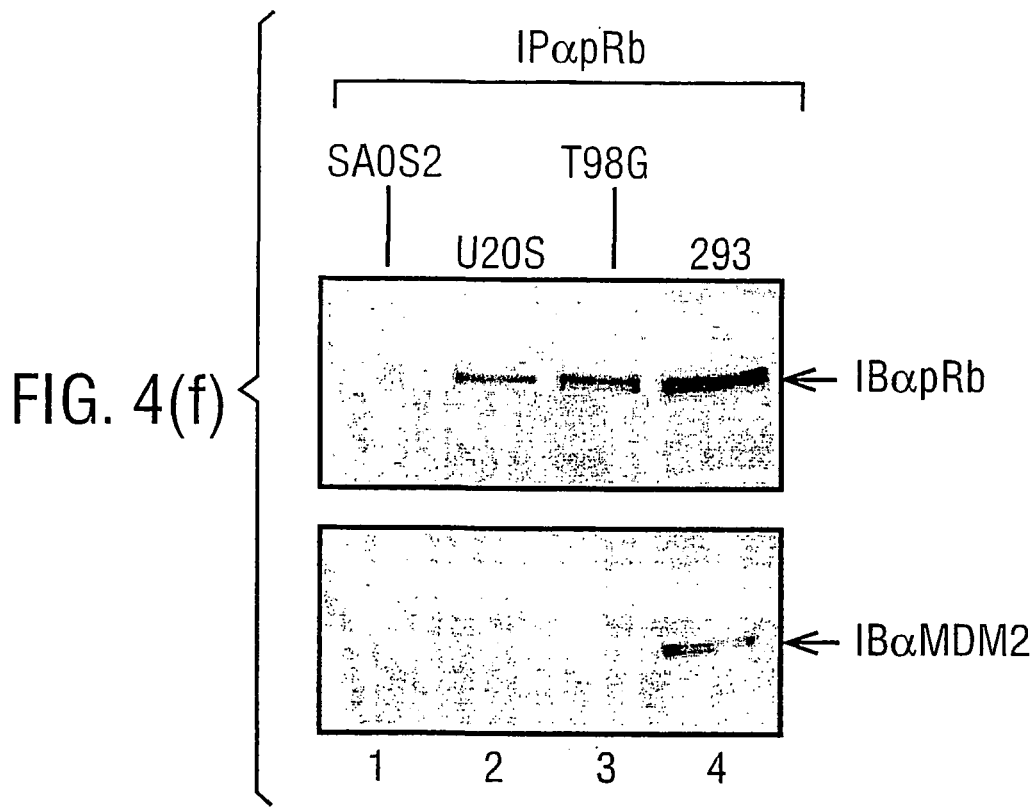

If the acetylation of pRb facilitates its interaction with MDM2, we would predict that the pRb/MDM2 complex should be detectable in a cell-type in which a high level of pRb acetylation was apparent. To test this idea, we compared the levels of the pRb/MDM2 complex in 293 cells, in which pRb is acetylated, to other cells where pRb acetylation could not be detected (FIG. 4d). Significant levels of human MDM2 were detectable in pRb immunoprecipitates performed from 293 cells, but undetectable in the other cell-types under study (FIG. 4f). This result is consistent with the conclusion that acetylated pRb binds efficiently to MDM2, and the presence of acetylated pRb in 293 cells.

Figure 4G:
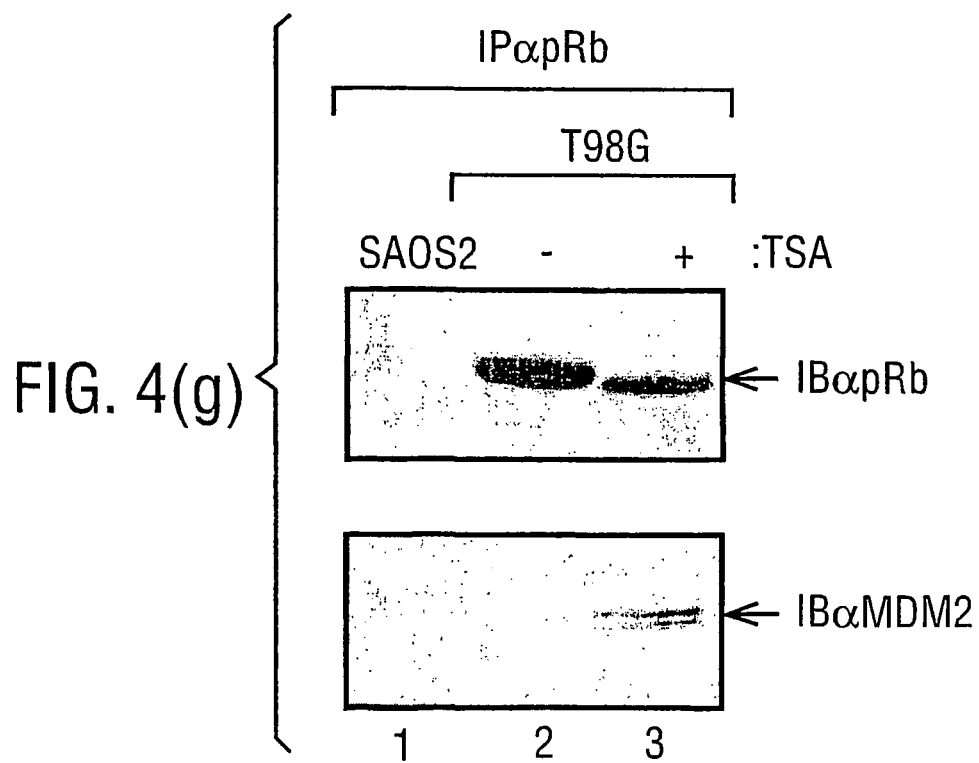

Conversely, conditions that enhance acetylation would be expected to promote the interaction of pRb with MDM2. To this end, we treated T98G cells with trichostatin A (TSA), which blocks histone deacetylase (HDAC) activity 18 and thereafter assessed the interaction between pRb and MDM2. Whereas the pRb/MDM2 complex was not apparent in T98G cells, it was clearly detectable in extracts prepared from T98G cells treated with TSA (FIG. 4g). Overall, these results are consistent with the idea that acetylation influences the interaction between pRb and MDM2.

G. Lys 873 and 874 of pRb are Targets for Acetylation.

Figure 5A:
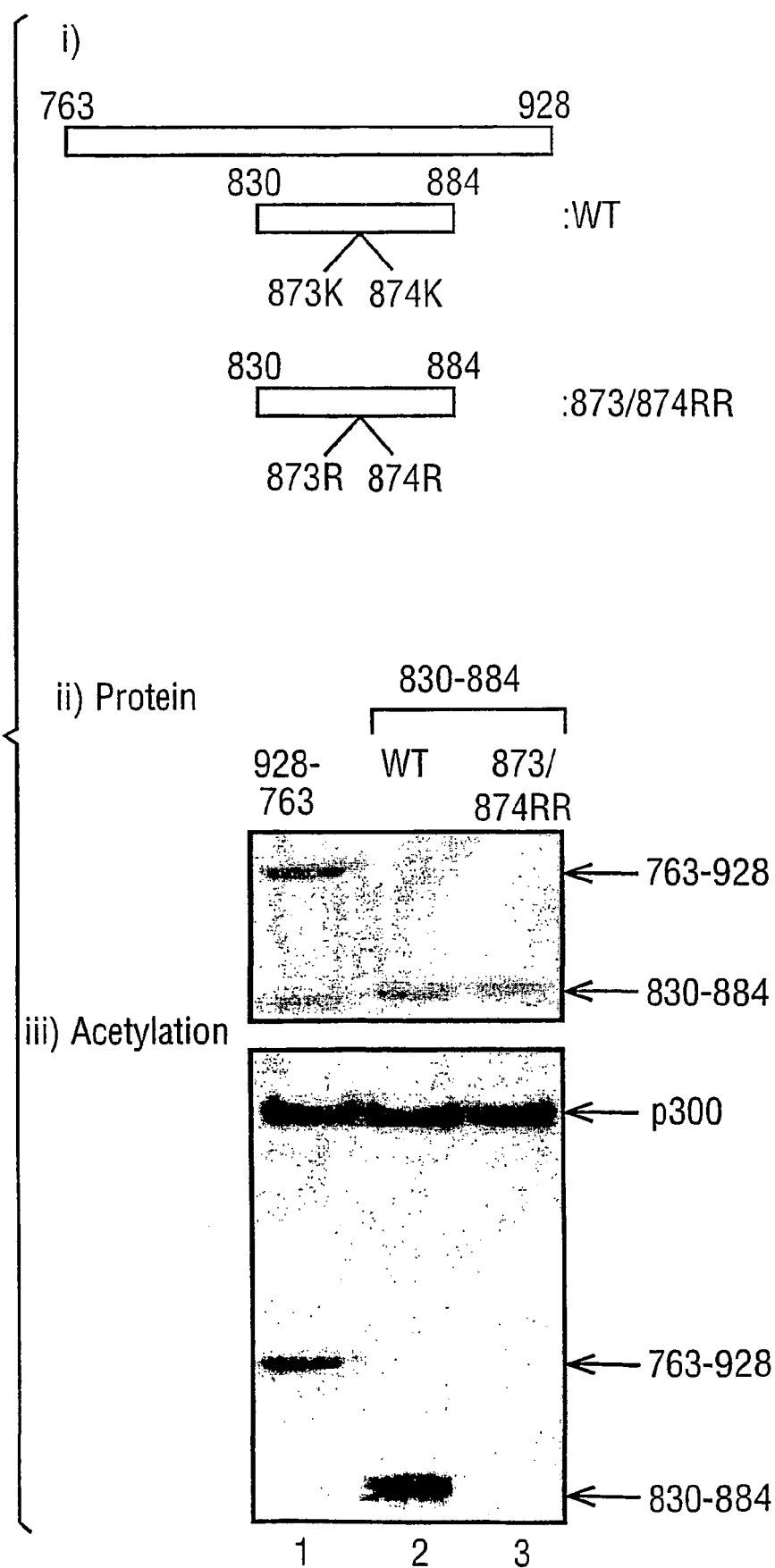

To further clarify the role of acetylation in pRb, we identified lysine residues that are directly acetylated by the p300 HAT and thereafter assessed their functional importance for wild-type pRb. We focussed our attention on the C-terminal region between residue 830 and 884, which contains five lysine residues and is acetylated by p300 HAT (FIG. 2e). By systematically altering individual lysine to arginine residues by site-directed mutagenesis, we identified lysines 873 and 874 within a lysine rich region as subject to acetylation (FIG. 5a). Thus, acetylation of pRb from residue 830 to 884 was lost upon altering residues 873 and 874 to arginine (FIG. 5a). In turn, this observation suggests that the remaining three lysine residues within this region of pRb are unlikely to be acetylated by p300 HAT.

H. Acetylation of pRb Reduces Phosphorylation by cdks.

Figure 5B:
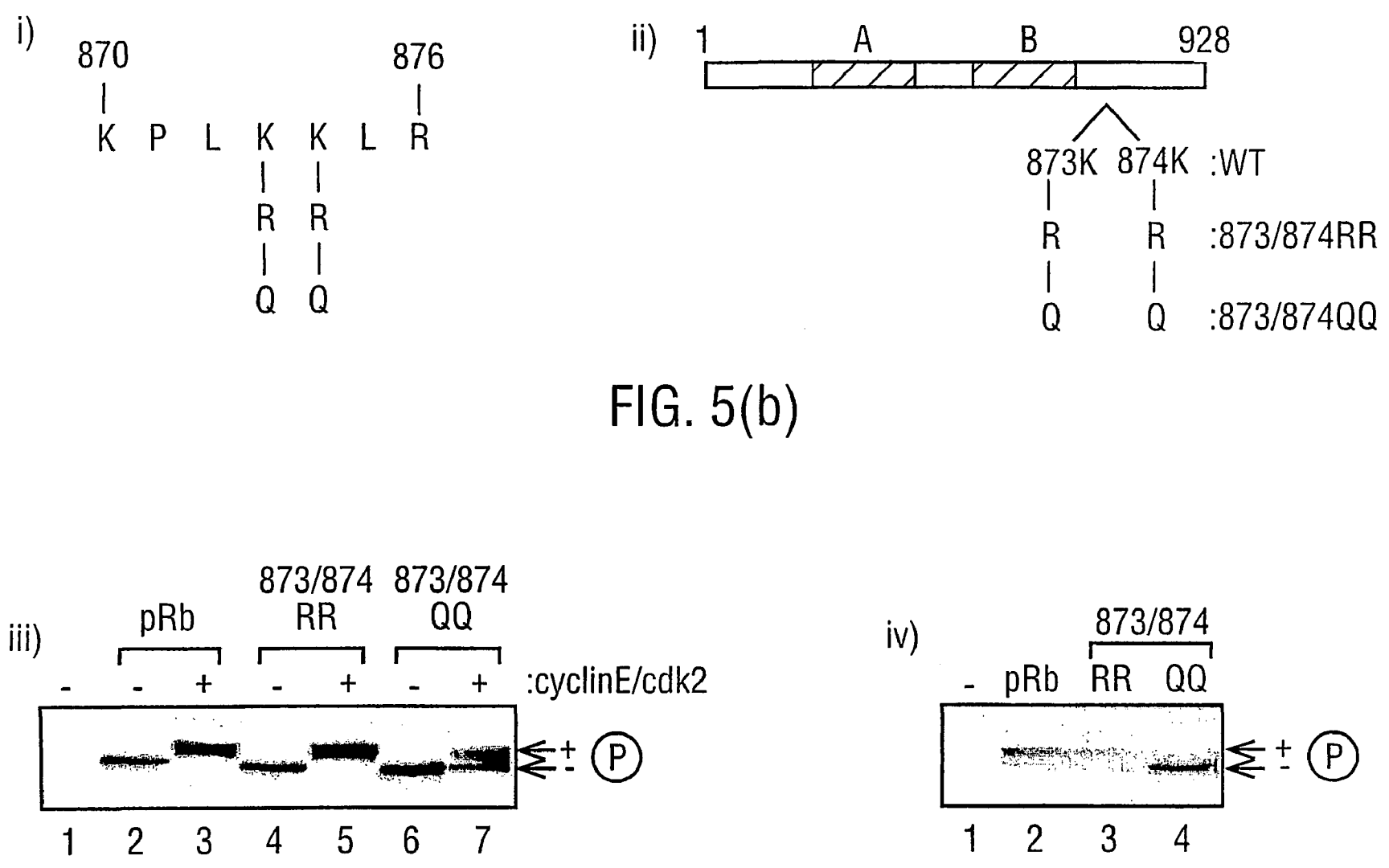

As we were interested to determine the functional importance of acetylation in pRb we considered that acetylation may influence pRb phosphorylation, which provides a major level of control in regulating pRb activity [1, 2]. Furthermore, the C-terminal region between residue 830 to 884 has been suggested to contain a motif that influences pRb phosphorylation by cyclin-dependent kinases (cdk) [19]. To test this idea, we introduced 873/874RR into wild-type pRb and thereafter assessed phosphorylation of the 873/874RR mutant by cyclin E/cdk2, which acts during the G1 phase to phosphorylate pRb [1, 3]. In addition, we prepared 873/874QQ in which lysine residues 873/874 were altered to glutamine residues (FIG. 5b). In contrast to 873/874RR, where the arginine residue retains the basic charge of the lysine residue but cannot be acetylated, a change to a glutamine residue would be anticipated to mimic the acetylation status of the lysine residue [20]. In SAOS2 cells both wild-type pRb and 873/874RR were phosphorylated to an equivalent level by exogenous cyclin E/cdk2, whereas 873/874QQ failed to reach a comparable level of phosphorylation (FIG. 5biii). A similar analysis was performed in U2OS cells which contain high levels of endogenous cdk activity. As for SAOS2 cells, both wild-type pRb and 873/874RR were phosphorylated to an equivalent level, whereas 873/874QQ was significantly reduced (FIG. 5biv). These results suggest that the acetylation of pRb on lysine residue 873 and 874 influences the phosphorylation control of pRb activity.

I. Acetylation Provides a New Level of pRb Control.

The acetylation of pRb described here suggests a new level of control in the regulation of pRb activity, and a novel mechanism of action through which viral oncoproteins can overcome tumour suppressor activity. Whilst the acetylation of nucleosomes is recognised to play an important role in regulating chromatin accessibility [5, 6, 18], and some DNA binding transcription factors are known to be acetylated [13, 14, 21, 22, 23, 24], to our knowledge the acetylation control of pRb provides the first example of an acetylation-regulated and cell cycle-relevant protein-protein interaction. Our findings point towards a mechanism whereby E1A can direct the p300 HAT activity to enzymatically modify pRb and thereafter alter pRb function (FIG. 6), thus suggesting that E1A can act as a targeting subunit for a cellular HAT activity which thereafter enforces altered growth-control.

Since the p300-binding domain in E1A is necessary for some of the physiological effects ascribed to E1A, such as the induction of DNA synthesis and inhibition of differentiation [3], and p300 may function in proliferation control in normal cells [5], it is a possibility that the ability of E1A to stimulate pRb acetylation is responsible for some of the effects previously ascribed to the p300-binding domain [3, 25].

In this respect, our results imply that pRb acetylation influences the interaction with the MDM2 oncoprotein, which may subsequently allow MDM2 to exert some of its oncogenic growth-promoting effects through the release of E2F activity [7]. Thus, the ability of E1A to stimulate pRb acetylation and thereafter MDM2 binding to pRb would be expected to translate into a pathway that augments cell cycle progression.

J. Acetylation of pRb may Counterbalance HDAC Activity.

It is noteworthy that HDAC binds to pRb, and may contribute to pRb-dependent growth control [26]. An interesting possibility is that the acetylation of pRb may to a certain extent be counterbalanced by HDAC, thus maintaining pRb in a hypo-acetylated state. It is consistent with this idea that we also found that HDAC can efficiently deacetylate pRb, and further that TSA treatment which blocks HDAC activity augments the interaction between pRb and MDM2 (FIG. 4).

K. Conclusions.

In addition to the above, it is of considerable interest that the acetylation of pRb may influence the ability of phosphorylation by cdk kinases to modulate pRb tumour suppressor function. We note that lysine residues 873 and 874 are part of a previously identified cdk docking site [19] which, if the properties of such a site were to be modulated by acetylation, provides a plausible mechanism for the influence of acetylation on pRb phosphorylation. The data presented here support the idea that the acetylation of pRb impedes subsequent phosphorylation by cdk kinases, implying perhaps that the acetylation control of pRb may be a regulatory pathway that acts in a fundamentally distinct fashion to that of pRb phosphorylation.

Figure 6:
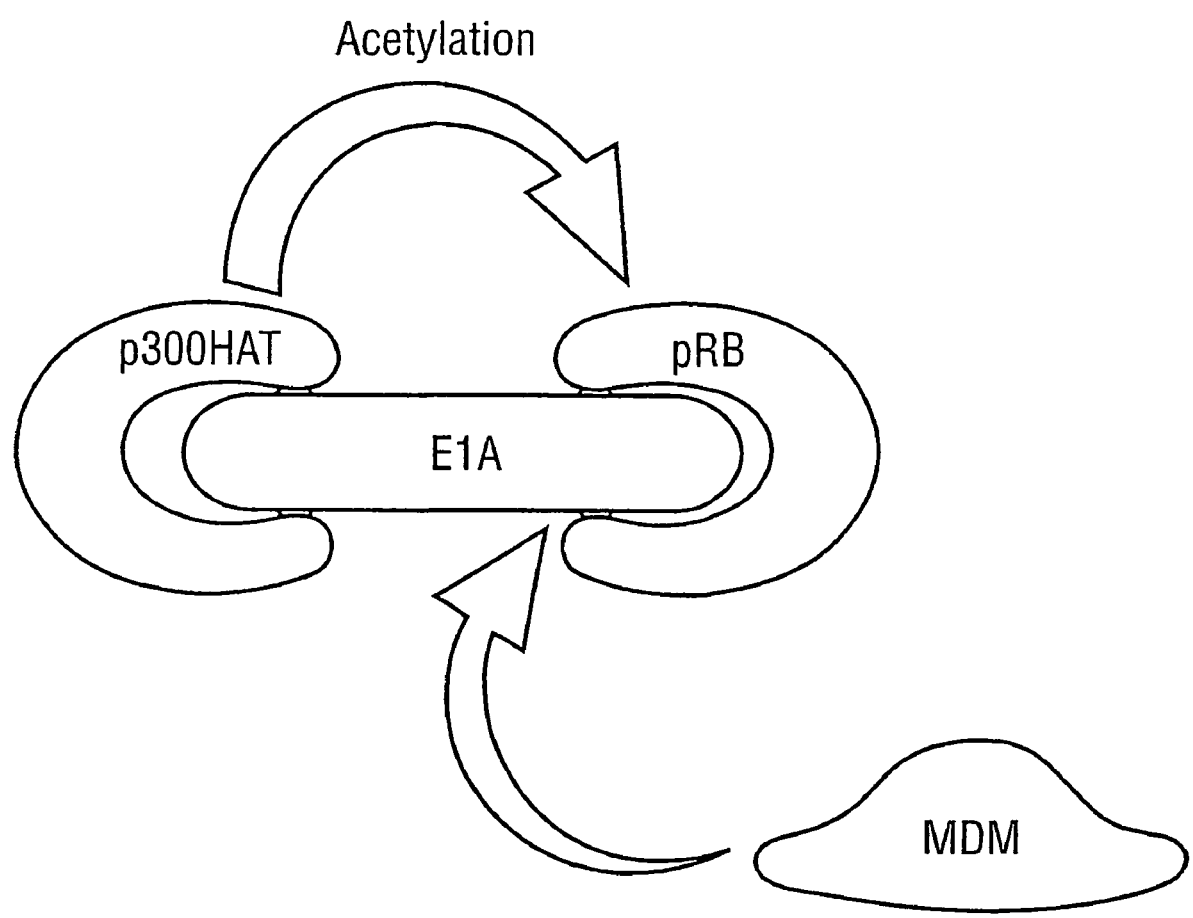
FIG. 6 is an overview of acetylation control of pRb activity.

In conclusion, our results suggest a rationale for the sequestration of p300 by E1A, namely in directing a cellular enzyme to the control of tumour suppressor activity (FIG. 6). These observations therefore establish a novel relationship between p300, pRb and acetylation in which E1A acts as an enzyme targeting subunit in an enzyme-substrate-type of relationship, thus favouring the enzymatic modification of pRb in a fashion that contributes to a loss of pRb-dependent growth control.

Material and Methods.

Plasmids.

pGEX-Rb, Δ21 and Δ22 mutants, pGEX-Rb 763-928, pGEX-Rb 794-829, 844, 857, 864, 876, 884, 896, 910 were as previously described [9, 19]. pGEX-Rb 830-884, 830-928, 881-928, and 641-775 were cloned by direct PCR (see primers below) from pcDNA3-9E10-Rb, and pGEX-Rb 379-656 contained the Nhe1 to EcoR1 fragment from pGEX-Rb9. pGEX E1A, pm928 and Δ36 were cloned by PCR (see primers below) from pCMV-E1A, pCMV-E1Apm928 or pCMV-E1AΔ2-36 [16, 27]. The His-p3001195-1673 and Flag-p3001135-2414 bacterial expression vector and Flag-p300 (wild-type) were as described [28, 29]. pcDNA-MDM2 has been described [30].

| Plasmids | 5'-primer | 3'-primer |
|---|---|---|
| GST-Rb (830–884) | 5'-cgggatccagaatcttagtatcaattgg-3' (SEQ ID NO:1) | 5'-cggaattctcattcatctgatccttcaatatc-3' (SEQ ID NO:2) |
| GST-Rb (830–928) | 5'-cgggatccagaatcttagtatcaattgg-3' (SEQ ID NO:3) | 5'-cggaattctcatttctcttccttgtttg-3' (SEQ ID NO:4) |
| GST-Rb (881–928) | 5'-cgggatccggatcagatgaagcagatg-3' (SEQ ID NO:5) | 5'-cggaattctcatttctcttccttgtttg-3' (SEQ ID NO:6) |
| GST-Rb (641–775) | 5'-ccattgaaatctacctctc-3' (SEQ ID NO:7) | 5'-tcacctggtggaagcatacctgc-3' (SEQ ID NO:8) |

-continued

| Plasmids | 5'-primer | 3'-primer |
|---|---|---|
| GST-E1A | 5'-cgggatccatgagacatattatctgccac-3' (SEQ ID NO:9) | 5'-ccctcgagttatggcctggggcgtttac-3' (SEQ ID NO:10) |
| GST-E1A (ΔN36) | 5'-cgggatcccattttgaaccacctacc-3' (SEQ ID NO:11) | 5'-ccctcgagttatggcctggggcgtttac-3' (SEQ ID NO:12) |

In Vitro Protein Acetylation Assay.

PAGE analysis of protein acetylation was performed as described [29], with slight modification. The indicated amounts of input proteins were incubated at 30 C for 45-60 min in 30 μl of volume with 5×HAT assay buffer (250 mM Tris pH 8.0, 25% glycerol, 0.5 mM EDTA, 250 mM KCl, and 10 mM sodium butyrate), 90 pmol [14C]acetyl CoA (55 mCi/mol, Amersham Life Science Inc.) and the appropriate amount of water to a final volume of 30 μl. After incubation, reactions were stopped by adding 15 μl of 3×SDS loading buffer (150 mM Tris-HCl (pH 6.8), 6% SDS, 30% glycerol, 0.3% bromophenol blue, 3% mercaptoethanol), and analysed on SDS-PAGE. The gels were dried and exposed for autoradiography for 48-96 h. Quantitation of acetylation was performed by phosphoimaging.

Expression and Purification of Glutathione-S-transferase Fusion Proteins.

Glutathione-S-transferase fusion protein expression and purification was performed as recommended by the manufacturer (Pharmacia). Fresh overnight cultures of BL21 (DE3) pLys (Invitrogen) transformed with the appropriate pGEX-recombinants were diluted 1:10 in Luria-Bertani (LB) medium containing ampicillin (100 μg/μg) and incubated at 37° C. with shaking. After 2 h of growth, isopropyl-β-D-thiogalactopyranoside (IPTG, Sigma) was added to final concentration of 0.5 mM The cultures were subsequently incubated at 30 C for 4-5 h for protein expression before harvesting.

For fusion protein purification using glutathione-Sepharose (Pharmacia), bacterial cultures were pelleted by centrifugation at 6,000 rpm for 10 min at 4 C. The pellets were resuspended in cold PBS (Sigma, 5 ml PBS/100 ml of bacterial culture). The bacteria were then lysed on ice by mild sonication and Triton-X-100 (Sigma) was added to the lysate to a final concentration of 1%. The lysate was incubated at 4 C for 30 min, then centrifuged at 13,000 rpm, 4 C for 30 min. The bacterial supernatants were rocked for 30-45 min at 4 C with glutathione-Sepharose (200 μl of beads/100 ml culture). The glutathione-Sepharose beads were washed three times with 20 ml of cold PBS supplemented with 1% of Triton, and once with 20 ml of cold PBS. For the analysis of bound proteins, the appropriate amount of beads were boiled in 1× sample buffer (50 mM Tris-HCl (pH 6.8), 2% SDS, 10% glycerol, 0.1% bromophenol blue, 1% mercaptoethanol), and loaded onto an SDS-polyacrylamide gel. Proteins were visualized by Coomassie blue staining. To elute the GST-fusion proteins from beads, proteins were eluted in elution buffer (50 mM Tris-HCl (pH 8.0), 10 mM reduced glutathione, 120 mM NaCl). All fusion proteins were subsequently dialysed into BC100 buffer (20 mM Tris-HCl (pH 8.0), 0.5 mM EDTA, 100 mM KCl, 20% glycerol, 0.5 mM DTT, 0.5 mM PMSF).

Expression and Purification of His-tagged Fusion Proteins.

The procedure for His-tagged fusion protein purification was similar to the GST-fusion protein purification. Briefly, 5 ml of PBS (supplemented with 0.5M NaCl, 10 mM imidazole pH 7.4 and protease inhibitor cocktail (Calibiochem)) was used to resuspend the bacterial pellet from 100 ml culture. The bacteria were then lysed on ice by mild sonication and pelleted at 13,000 rpm for 30 min at 4 C. The supernatant was collected and incubated with Ni-NBT agarose (QIAGEN) at 4 C for 1 h. After incubation, the beads were washed 5 times in PBS (supplemented with 0.5M NaCl, 40 mM imidazole pH 7.4). Elution was carried out using BC100 buffer supplemented with 200 mM imidazole.

Production of Flag-p3001135-2414 Baculovirus.

To generate the baculovirus vector for Flag-p3001135-2414, the BAC-To-BAC Baculovirus Expression system from Gibco Life Technologies was used. In short, Flag-p3001134-2414 sequence was taken out from the bacterial expression vector [34] by RsrII and NotI digest. The fragment isolated was cloned directly into the RsrII and NotI sites of pFastBacHTa vector to generate the baculovirus vector expressing Flag-p3001135-2414.

Expression and Purification of Flag-p300 from sf9 cells.

To express flag-p300 in sf9 cells, 1.5×107 sf9 cells were infected with the appropriate baculovirus at multiplicity of infection of 10. The sf9 cells were harvested for protein purification after 48 h of incubation at 25 C. The method of purification was essentially as described [31]. The sf9 cells were pelleted by mild centrifugation at 700 rpm and washed twice with cold PBS. The sf9 cells were lysed in 2 ml of HEMG buffer (25 mM Hepes-KOH (pH 7.6), 0.1 mM EDTA, 12.5 mM MgCl2, 10% glycerol) supplemented with 400 mM KCl, 0.1% NP-40 and protease inhibitor cocktail (Calibiochem). The samples were quickly freeze-thawed three times and centrifuged at 13,000 rpm at 4 C for 30 min. The supernatant was collected and incubated with anti-flag M2 affinity gel (Sigma, 200 μl of beads/ml of supernatant), in HEMG buffer containing 200 mM KCl. After 2 h of incubation at 4 C, the beads were washed 5 times with HEMG buffer supplemented with 200 mM KCl. Proteins bound on the beads were elute in elution buffer which is basically HEMG buffer supplemented with 160 mM KCl and 1 mg/ml of flag-peptide (Sigma). Elution was carried out at 4 C for 2 h. Proteins elute were analysed by SDS-PAGE and visualized by Coomassie blue staining.

Tissue Culture and Transfection.

The C33A, U2OS, SAOS2, T98G, HEK293, and A31 cells were all cultured in Dulbecco modified Eagle medium (Gibco) supplemented with 10% foetal bovine serum at 37 C in 5% $CO_2$. Transfections were carried out using calcium phosphate method as described [32].

Western Blot and Immunoprecipitation.

The following antisera were used; anti-Ac-Lys (New England Biolabs), anti-Ac-H4 (Serotec), anti-Rb monoclonal IF8, G3-245 (Pharmingen) and C15 (Santa Cruz), anti-p300 N15 (Santa Cruz) and anti-MDM2H221 (Santa Cruz).

For immunoprecipitation of endogenous acetylated pRb, cell pellets collected from SAOS2, U2OS, T98G, A31, and HEK293 cells were lysed in IPH buffer (50 mM Tris pH 8.0, 150 mM NaCl, 0.5% NP-40, protease inhibitor cocktail (Roche), 5mM EDTA, 5 µM TSA (Sigma)). The protein concentration of the extracts was determined by Bradford assay (BioRad). Protein-A-agarose was first incubated with anti-Rb antibody IF8 and C15 for 1-2 h at 4 C. The beads were washed 3 times with IPH buffer, and incubated with cell extracts overnight at 4 C. Proteins bound to the beads were elute with 3×SDS loading buffer and analysed by Western blotting using appropriated antibodies. To immunoprecipitate pRb from transfected cells, SAOS2 cells were transfected with pcDNA3-Rb or empty vector as described 32 and, after 48 h, harvested and immunoprecipitated with IF8 and C15.

In vitro Binding Assay Between Rb and MDM2.

About 2 µg of GST-Rb was acetylated by Flag-p300 in a standard 30 µl reaction as described above, but using 1 µl of 10 mM cold acetyl-CoA. For the unacetylated Rb sample, the acetylation reaction was carried out without acetyl-CoA. After completion of the acetylation reactions, the reaction was incubated with Flag beads (Sigma) in 400 µl of IPH buffer to remove Flag-p300. The supernatant was collected and immunoprecipitated with protein-A-agarose as described above with either anti-Ac-Lys antibody or anti-Rb antibody (C15 and IF8) to purify the acetylated Rb and unacetylated Rb respectively; the anti-acetylated lysine antibody failed to recognise the unacetylated pRb (FIG. 1c). In vitro transcribed and translated MDM2 was incubated with equal amounts (determined by immunoblotting) of acetylated or unacetylated Rb to access binding efficiency. After incubation, the beads were washed three times with IPH buffer (containing 0.25% NP-40), and samples analysed on SDS-PAGE followed by Western blot analysis with the MDM2 antibody H221.

Site-Directed Mutagenesis and Transfection.

Site-directed mutagenesis was performed using Quick-change (Strategene). PCR was performed using pcDNA3-9E10 Rb to create pcDNA3-Rb (873/874RR) and pcDNA-Rb (873/874QQ), and pGEX-Rb 830-884 to generate pGEX-Rb 830-884/873/874RR. All constructs were confirmed by sequencing. Transfection into SAOA2 and U2OS cells in the presence or absence of cyclin E/cdk2 kinase and immunoblotting was carried out as previously described [32].

DETAILED DESCRIPTION OF THE FIGURES

FIG. 1

The retinoblastoma Protein is Modified by Acetylation.
a) Schematic representation of GST-pRb, pRbΔ21 and pRbΔ22 used in the acetylation assays.
b) i) The indicated GST-pRb derivatives were expressed, purified and analysed on an SDS gel. The gel was stained with coomassie blue.
   ii) The indicated GST proteins (2 µg) were incubated with his-tagged p3001195-1673 (about 0.5 µg) and 14C acetyl CoA as described and analysed by SDS PAGE.
c) GST-pRb (2 µg) was incubated with Flag-tagged p3001135-2414 (0.3 µg) in the presence or absence of acetyl CoA as indicated. After incubation, 1/10 of the reaction was loaded onto tracks 1 and 3, and 9/10 of the reaction onto 2 and 4. The upper panel shows an immunoblot performed with the anti-pRb C15 polyclonal antibody and the lower panel an immunoblot performed with anti-acetyl lysine antisera.
d) SAOS2 (Rb–/–) cells were transfected with pCMV-Rb (30 µg; tracks 2, 4, 5 and 6; indicated by +) or the empty vector pCMV (30 µg; tracks 1 and 3; indicated by –) as described. At 48 h, cell extracts were prepared and immunoprecipitated with anti-pRb monoclonal antibody (tracks 1, 2, 3 and 4) or a control monoclonal antibody (tracks 5 and 6). Samples were resolved by SDS PAGE and immunoblotted with either anti-pRb monoclonal antibodies (tracks 1, 2 and 6) or the anti-acetyl lysine antisera (tracks 3, 4 and 5); pRb is indicated.
e) Extracts prepared from 293 cells were immunoprecipitated with anti-pRb (C15 and IF-8; tracks 2 and 5) or control antibodies (tracks 3 and 6), and after electrophoresis, immunoblotted with either anti-pRb monoclonal antibody G3-245 (tracks 2 and 3) or anti-acetyl lysine antisera (tracks 5 and 6). Tracks 1 and 4 show that input 293 extract immunoblotted with either anti-pRb or anti-acetyl lysine.

FIG. 2

The C-Terminal Region of pRb is a Major Site of Acetylation.

The indicated derivatives of pRb (a, c and e) were expressed and purified as GST-fusion proteins and analysed on an SDS gel (bi and di). Each GST-pRb derivative (2 to 3 µg) was assessed for in vitro acetylation by Flag-tagged p3001135-2414 (0.3 µg) in the presence of 14C acetyl CoA as described (bii, dii and f). Acetylated pRb and auto-acetylated p300 is indicated (bii, dii and f), and GST alone input is shown (bi; track 1 with the GST protein indicated by *. Note that the Rb(A) fragment shows a low level of acetylation (bii, track 3).

FIG. 3

Adenovirus E1A Augments the p300-Dependent Acetylation of the pRb Protein.
a) In vitro acetylation assay in which the indicated recombinant proteins (coomassie blue stained gel shown in i)) were assessed for level of acetylation (shown in ii) in the presence of 14C acetyl CoA. An equal amount of Flag-tagged p3001135-2414 (0.3 µg) was used throughout, together with GST-pRb (2 µg; tracks 1, 2 and 3) or GST-E2F-1 (2 µg; tracks 4, 5 and 6) and increasing His-E1A13S (0.3 or 1 µg in tracks 2 and 5, and 3 and 6 respectively). The same gel is shown, representing protein levels in i) and 14C acetylation in ii).
b) In vitro 14C acetylation assay in which Flag-tagged p3001135-2414 (0.3 µg) together with increasing His-E1A13S (0.3 or 1 µg in tracks 2 and 3 respectively) was incubated with purified chicken core histones (1 µg; tracks 1, 2 and 3). The same gel is shown, representing protein levels in i) and 14C acetylation in ii).
c) In vitro 14C acetylation assay to compare the effect of E1A on pRb (i) and p53 (ii) acetylation, in which Flag-tagged p3001135-2414 (0.3 µg) was incubated with either wild-type GST-tagged pRb (1.0 µg; i)) or GST-p53 (0.5 µg; ii) in the presence of increasing levels of GST-E1A12S (0.04, 0.2, 1 or 5 µg in tracks 2 to 5). In track 6, the effect of GST (5 µg) is shown. Note that the assays shown in i) and ii) were performed in parallel in the same experiment.

FIG. 4

Domains in E1A for p300-Dependent Acetylation of pRb and Acetylated pRb Binds to MDM2.
a) In vitro acetylation assay in which Flag-tagged p3001135-2414 (0.3 µg) together with GST-pRb (2 µg) was incubated with either wild-type GST-E1A, GST-Δ36 or GST-pm928 (1 μg) as indicated. The effect of the buffer (track 5) or GST (1 μg; track 1) alone was also assessed. The quantification of the level of p300 autoacetylation (b) and pRb acetylation (c) in the presence of the E1A derivatives is shown. The highest level of acetylation was given an arbitrary value of 100. E1A derivatives GST-ΔCR1 and GST-ΔCR2 failed to stimulate pRb acetylation, and • indicates a polypeptide that is likely to be a derivative of p300.

b) Extracts prepared from the indicated cells (SAOS2, A31, U2OS, T98G and 293) were immunoprecipitated with anti-pRb (C15 and IF-8) antibodies and, after electrophoresis, immunoblotted with either anti-pRb G3-245 (top), anti-p300 N15 (middle) or anti-acetylated lysine (bottom) antisera. Note that although equivalent levels of pRb are immunoprecipitated from the different cell extracts, only 293 cells (which express E1A), contain high levels of p300 (middle) and acetylated pRb (bottom) in the immunocomplex; C15 and IF8 do not immunoprecipitate murine pRb in A31 cells.

c) GST-pRb was acetylated with Flag-p300 (wild-type) and thereafter Flag-p300 removed. The binding of in vitro translated MDM2 to non-acetylated (track 2) or acetylated pRb (track 3) was assessed as described followed by immunoblotting with anti-MDM2. The input MDM2 is shown in track 1, and tracks 4 and 5 show the input (5%) GST-pRb with (track 5) or without (track 4) acetylation determined by immunoblotting with anti-pRb (G3-245). Note that the binding of MDM2 to acetylated pRb was much more efficient than the binding activity for non-acetylated pRb.

d) Extracts prepared from the indicated cells (SAOS2, U2OS, T98G and 293) were immunoprecipitated with anti-pRb (C15 and IF-8) antibodies and, after electrophoresis, immunoblotted with either anti-pRb G3-245 (top) or anti-MDM2 (bottom) monoclonal antibody. Note that a high level of co-immunoprecipitated MDM2 is seen in the pRb immunocomplex only from 293 cell extracts, and that U2OS and T98G cells show very low but detectable levels (after longer exposure) of co-immunoprecipitated MDM2.

e) Extracts prepared from T98G cells either treated with or without TSA (5 μM) for 18-20 h, and untreated SAOS2 cells were immunoprecipitated with anti-pRb (C15 and IF8) antibodies and after electrophoresis immunoblotted with either anti-pRb G3-245 (top) or anti-MDM2 (bottom) monoclonal antibody. Note the presence of MDM2 in the pRb immunocomplex from TSA-treated T98G cells.

FIG. 5

Functional Effects of pRb Acetylation.

a) In vitro acetylation of the indicated GST derivatives (2 μg) of pRb, namely pRb763-928, pRb830-884 and 873/874RR (i) after expression and purification as GST proteins (ii) and 14C acetylation (iii) with Flag-tagged p3001135-2414 (0.3 μg).

b) In vivo phosphorylation of the indicated derivatives of full-length pRb, namely wild-type pRb, 873/874RR and 873/874QQ (ii) after transfection into SAOS2 (iii) or U2OS (iv) cells of pcDNA3-9E10Rb, pcDNA3-Rb (873/874RR) or pcDNA3-Rb (873/874QQ) (10 μg) in the presence of exogenous cyclin E/cdk2 (4 μg of each vector [33]; indicated by +). After 24 h of transfection, extracts were prepared, quantitated, and immunoblotted with anti-pRb (G3-245). The position of hyper (+) and hypo (−) phosphorylated (P) pRb is indicated. i) shows the sequence surrounding lysine 873/874 as previously noted 19.

FIG. 6

Acetylation Control of pRb Activity.

It is envisaged that the E1A oncoprotein recruits p300 and pRb into a ternary complex to facilitate the p300-dependent acetylation of pRb. The results suggest that the acetylation of pRb favours the interaction with MDM2, which thereafter releases E2F from pRb control. Subsequently, E2F is able to promote cell cycle progression.

REFERENCES

1. Weinberg, R. A. (1995) The retinoblastoma protein and cell control. Cell 81, 323-330.
2. Dyson, N. (1998) The regulation of E2F by pRb-family proteins. Genes Dev. 12, 2245-2262.
3. Dyson, N. and Harlow, E. (1992) Adenovirus E1A targets key regulators of cell proliferation. Cancer Surv. 12, 161-195.
4. Sherr, C. J. (1996) Cancer cell cycles. Science 274, 1672-1677.
5. Shikama, N., Lyon, J. and La Thangue, N. B. (1997) The p300/CBP family: integrating signals with transcription factors and chromatin. Trends Cell Biol. 7, 230-236.
6. Brown, C. E., Lechner, T., Howe, L. and Workman, J. L. (2000) The many HATs of transcription co-activators. Trends Biol. Sci. 25, 15-18.
7. Xiao, Z.-X., Chen, J., Levine, A. J., Modjtahedi, N., Xing, J., Sellers, W. R. and Livingston, D. M. (1995) Interaction between the retinoblastoma protein and the oncoprotein MDM2. Nature 375, 964-698.
8. Martin, K., Trouche, D., Hagemeier, C., Sorensen, T. S., La Thangue, N. B. and Kouzarides, T. (1995) Stimulation of E2F1/DP1 transcriptional activity by MDM2 oncoprotein. Nature 375, 691-694.
9. Bandara, L. R., Adamczewski, J. P., Hunt, T. and La Thangue, N. B. (1991) Cyclin A and the retinoblastoma gene product complex with a common transcription factor. Nature 352, 249-251.
10. Yang, X.-J., Ogryzko, V. V., Nishikawa, J.-I., Howard, B. H. and Nakatani, Y. (1996) A p300/CBP-associated factor that competes with the adenoviral oncoprotein E1A. Nature 382, 319-324.
11. Arany, Z., Newsome, D., Oldread, E., Livingston, D. M. and Eckner, R. (1995) A family of transcriptional adaptor proteins targeted by the E1A oncoprotein. Nature 374, 81-84.
12. Gu, W. and Roeder, R. G. (1997) Activation of p53 sequence-specific DNA binding by acetylation of the p53 C-terminal domain. Cell 90, 595-606.
13. Sakaguchi, K., Herrera, J. E., Saito, S.-i., Miki, T., Bustin, M., Vassilev, A., Anderson, C. W. and Appella, E. (1998) DNA damage activates p53 through a phosphorylation-acetylation cascade. Genes Dev. 12, 2831-2841.
14. Martinez-Balbás, M. A., Bauer, U-M., Nielsen, S. J., Brehm, A. and Kouzarides, T. (2000) Regulation of E2F-1 activity by acetylation. EMBO J. 19, 662-271.
15. Marzio, G., Wagener, C., Gutierrez, M. I., Cartwright, P., Helin, K. and Giacca, M. (2000) E2F family members are differentially regulated by reversible acetylation. J. Biol. Chem. 275, 10887-10892.
16. Kraus, V. B., Moran, E. and Nevins, J. R. (1992) Promoter-specific trans-activation by the adenovirus E1A12S product involves separate E1A domains. Mol. Cell. Biol. 12, 4391-4399.

17. Lassam, N. J., Bayley, S. T. and Graham, F. L. (1979) Tumor antigens of human Ad5 in transformed cells and in cells infected with transformation-defective host-range mutants. Cell 18, 781-791.
18. Hassig, C. A. and Schrieber, S. L. (1997) Nuclear histone acetylases and deacetylases and transcriptional regulation: HATs off to HDACs. Curr. Opin. 1, 300-308.
19. Adams, P. D., Sellers, W. R., Sharma, S. K., Wu, A. D., Nalin, C. M. and Kaelin Jr., W. G. (1996) Identification of a cyclin-cdk2 recognition motif present in substrates and p21-like cyclin-dependent kinase inhibitors. Mol. Cell. Biol. 16, 6623-6633.
20. Zhang, W., Bone, J. R., Edmondson, D. G., Turner, B. M. and Roth, S. Y. (1998) Essential and redundant functions of histone acetylation revealed by mutation of target lysines and loss of the Gcn5p acetyltransferase. EMBO J. 17, 3155-3167.
21. Zhang, W. and Bieker, J. J. (1998) Acetylation and modulation of erythroid Krüppel-like factor (EKLF) activity by interaction with histone acetyltransferases. Proc. Natl. Acad. Sci. USA 95, 9855-9860.
22. Sartorelli, V., Puri, P. L., Hamamori, Y., Ogryzko, V., Chung, G., Nakatani, Y., Wang, J. Y. J. and Kedes, L. (1999) Acetylation of MyoD directed by pCAF is necessary for the execution of the muscle program. Mol Cell. 4, 725-734.
23. Boyes, J., Byfield, P., Nakatani, Y. and Ogryzko, V. (1998) Regulation of activity of the transcription factor GATA-1 by acetylation. Nature 396, 594-598.
24. Keirnan, R., Vanhulle, C., Schiltz, L., Adam, E., Xiao, H., Maudoux, F., Calomme, C., Burny, A., Nakatani, Y., Jeang, K.-T., Benkirane, M. and Van Lint, C. (1999) HIV-1 Tat transcriptional activity is regulated by acetylation. EMBO J. 18, 6106-6118.
25. Stein, R. W., Corrigan, M., Yaciul, P., Whelan, J. and Moran, E. (1990) Analysis of E1A-mediated growth regulation functions: binding of the p300-kilodalton cellular product correlates with E1A enhancer repression function and DNA synthesis-inducing activity. J. Virol. 64, 4421-4427.
26. Luo, R. X., Postigo, A. A. and Dean D. C. (1998) Rb interacts with histone deacetylase to repress transcription. Cell 92, 463-473.
27. Lee, C-W., Sorensen, T. S., Shikama, N. and La Thangue, N. B. (1998) Functional interplay between p53 and E2F through co-activator p300. Oncogene 16, 2695-2610.
28. Shikama, N., Lee, C-W., France, S., Delavaine, L., Lyon, J., Kristic-Demonacos, M. and La Thangue, N. B. (1999) A novel co-factor for p300 that regulates the p53 response. Mol. Cell 4, 365-376.
29. Ogryzko, V., Schiltz, R. L., Russanova, V., Howard, B. H. and Nakatani, Y. (1996) The transcriptional co-activators p300 and CBP are histone acetyltransferases. Cell 87, 953-959.
30. Loughran, Ö. and La Thangue, N. B. (2000) Apoptotic and growth-promoting activity of E2F modulated by MDM2. Mol. Cell Biol. 20, 2186-2197.
31. Chen, J-L. and Tjian, R. (1996) Reconstitution of TATA-binding protein-associated factor/TATA-binding protein complexes for in vitro transcription. Methods in Enzymology 273, 208-217.
32. Morris, L., Allen, K. E. and La Thangue, N. B. (2000) Regulation of E2F transcription by cyclinE/cdk2 kinase mediated through p300/CBP co-activators. Nature Cell Biol. 12, 232-239.

Although the foregoing invention has been described in some detail by way of illustration and example for the purposes of clarity and understanding, it will be readily apparent to those of skill in the art that certain changes and modifications may be made thereto without departing from the spirit or scope of the appended claims.

What is claimed is:

1. An assay for a modulator of acetylation of pRb by p300, which comprises
   a) bringing into contact a p300 protein, a pRb protein and a putative modulator compound under conditions where the p300 protein, in the absence of said modulator is capable of acetylating the pRb protein; and
   b) providing conditions for acetylation of said pRb protein;
   c) measuring the degree of inhibition of acetylation caused by said modulator compound.

2. An assay according to claim 1 wherein said pRb is in the form of a fusion protein with a detectable tag.

3. An assay according to claim 1 wherein the adenovirus E1A protein is present.

4. An assay according to claim 1 wherein the pRb is in the form of a C-terminal fragment of at least 40 amino acids comprising at least one target lysine residue.

5. An assay according to claim 1 wherein said p300 protein is a fragment of at least about 450 amino acids of a full-length p300, said fragment retaining the ability to acetylate pRb.

6. An assay according to claim 1 which is a cell based assay in which one or both of said p300 and pRb proteins are expressed using a recombinant DNA construct.

7. An assay according to claim 1 which further includes the step of phosphorylating the pRb protein using cyclinE/cdk2 as a means to determine the acetylation of pRb.

* * * * *